(12) United States Patent
Dorn et al.

(10) Patent No.: US 7,531,336 B2
(45) Date of Patent: May 12, 2009

(54) METHODS FOR PRODUCING RECOMBINANT HISTIDINE-TAGGED INOSINE NONOPHOSPHATE DEHYDROGENASE POLYPEPTIDES

(75) Inventors: Allan R. Dorn, Carmel, IN (US); Janice E. Rugaber, Indianapolis, IN (US)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 11/820,662

(22) Filed: Jun. 20, 2007

(65) Prior Publication Data

US 2008/0026424 A1    Jan. 31, 2008

Related U.S. Application Data

(62) Division of application No. 10/769,481, filed on Jan. 30, 2004, now Pat. No. 7,276,362.

(51) Int. Cl.
*C12N 9/02* (2006.01)
*C12P 21/06* (2006.01)
*C12N 1/20* (2006.01)
*C12N 15/00* (2006.01)
*C07H 21/04* (2006.01)

(52) U.S. Cl. ............ 435/189; 435/69.1; 435/183; 435/252.3; 435/320.1; 435/810; 536/23.2

(58) Field of Classification Search .............. None
See application file for complete search history.

(56) References Cited

U.S. PATENT DOCUMENTS

| | | | |
|---|---|---|---|
| 4,877,830 | A | 10/1989 | Dobeli et al. |
| 5,047,513 | A | 9/1991 | Döbeli et al. |
| 5,284,933 | A | 2/1994 | Dobeli et al. |
| 5,310,663 | A | 5/1994 | Dobeli et al. |
| 5,665,583 | A | 9/1997 | Collart et al. |
| 6,107,052 | A | 8/2000 | Dorn |
| 6,128,582 | A | 10/2000 | Wilson et al. |
| 6,147,194 | A | 11/2000 | Collart et al. |
| 6,479,628 | B1 | 11/2002 | Collart et al. |
| 6,524,808 | B1 | 2/2003 | Dorn et al. |
| 2002/0068346 | A1 | 6/2002 | Krystek et al. |

FOREIGN PATENT DOCUMENTS

| | | |
|---|---|---|
| DE | 198 11 313 | 9/1999 |
| EP | 1 207 394 A2 | 5/2002 |
| WO | WO 01/85952 A2 | 11/2001 |

OTHER PUBLICATIONS

Chica et al. Curr Opin Biotechnol. Aug. 2005;16(4):378-84.*
Colby, T.D., Vanderveen, K., Strickler, M.D., Markham, G.D., Goldstein, B.M., "Crystal structure of human type II inosine monophosphate dehydrogenase: Implications for ligant binding and drug design", Proc. Natl. Acad. Sci. USA, vol. 96, Mar. 1999, pp. 3531-3536.
Farazi, T., Leichman, J., Harris, T., Cahoon, M., Hedstrom, L., "Isolatoin and Characterization of Mycophenolic Acid-resistant Mutants of Inosine-5'-monophosphate Dehydrogenase", The Journal of Biological Chemistry, vol. 272, No. 2, Jan. 10, 1997, pp. 961-965.
Nimmesgern, E., Black, J., Futer, O., Fulghum, J.R., Chambers, S.P., Brummel, C.L., Raybuck, S.A., Sintchak, M.D., "Biochemical Analysis of the Modular Enzyme Inosine 5'-Monophosphate Dehydrogenase", Protein Expression and Purification 17, (1999) 282-289.
Schutz, E., Shipkova, M., Armstrong, V.W., Wieland, E., Oellerich, M. "Identification of a Pharmacologically Active Metabolite of Mycophenolic Acid in Plasma of Transplant Recipients Treated with Mycophenolate Mofetil", Clinical Chemistry 45, No. 3, 1999, 419-422.
Sintchak, M.D., Fleming, M.A., Futer, O., Raybuck, S.A., Chambers, S.P., Caron, P.R., Murcko, M.A., Wilson, K.P., "Structure and Mechanism of Inosine Monophosphate Dehydrogenase in Complex with the Immunosuppressant Mycophenolic Acid", Cell, vol. 85, Jun. 14, 1996, 921-930.
Mozo-Villarias, Angel et al., "A simple electrostatic criterion for predicting the thermal stability of proteins," Protein Engineering, vol. 16 No. 4 (2003) p. 279-286.
Shaw, Kevin L. et al., "The effect of net charge on the solubility, activity, and stability of ribonuclease Sa," Protein Science (2001) 10:1206-1215.
Sintchak, Michael D. et al., "Structure and Mechanism of Insoine Monophosphate Dehydrogenase in Complex with the Immunosuppressant Mycophenolic Acid," Cell, vol. 85, 921-930, Jun. 14, 1996.

* cited by examiner

*Primary Examiner*—Christian L Fronda
(74) *Attorney, Agent, or Firm*—Marilyn L. Amick; Roche Diagnostics Operations, Inc.

(57) ABSTRACT

The invention relates to a modified IMPDH polypeptide wherein the IMPDH polypeptide has a histidine tag and where the subdomain of the IMPDH polypeptide is modified so that the rate stability of the histidine-tagged, modified IMPDH polypeptide is maintained relative to the wild-type IMPDH polypeptide. The invention also relates to a method, nucleic acid molecules, vectors, and host cells for producing such a histidine-tagged, modified IMPDH polypeptide, and to kits comprising the histidine-tagged, modified IMPDH polypeptide.

24 Claims, 31 Drawing Sheets

5' GGA GAT ATA CAT ATG CAT CAC CAT CAC CAT CAC GCC GAC TAC C 3' (SEQ ID NO:1)

5' GGT AGT CGG CGT GAT GGT GAT GGT GAT GCA TAT GTA TAT CTC C 3' (SEQ ID NO:2)

5' GGT CCT CAG CCC CGA AGA TGA GGT GGA AGA TGT TTT TGA GGC
CGA AGC CGA GCA TGG TTT CTG C 3' (SEQ ID NO:3)

5' GCA GAA ACC ATG CTC GGC TTC GGC CTC AAA AAC ATC TTC CAC
CTC ATC TTC GGG GCT GAG GAC C 3' (SEQ ID NO:4)

5' CCA ATC ACA GAC ACA GGC GAA ATG GGG AGC GAG TTG GTG 3' (SEQ ID NO:5)

5' CAC CAA CTC GCT CCC CAT TTC GCC TGT GTC TGT GAT TGG 3' (SEQ ID NO:6)

5' GGC ATC ATC TCC TCC GAA GAC ATT GAT TTT CTC GAG GAG
GAG GAA C 3' (SEQ ID NO:7)

5' GTT CCT CCT CCT CGA GAA AAT CAA TGT CTT CGG AGG AGA
TGA TGC C 3' (SEQ ID NO:8)

Figure 3

```
atggccgact acctgattag tgggggcacg tcctacgtgc cagacgacgg actcacagca    60
cagcagctct tcaactgcgg agacggcctc acctacaatg actttctcat tctccctggg   120
tacatcgact tcactgcaga ccaggtggac ctgacttctg ctctgaccaa gaaaatcact   180
cttaagaccc cactggtttc ctctcccatg gacacagtca cagaggctgg gatggccata   240
gcaatggcgc ttacaggcgg tattggcttc atccaccaca actgtacacc tgaattccag   300
gccaatgaag ttcggaaagt gaagaaatat gaacagggat tcatcacaga ccctgtggtc   360
ctcagcccca aggatcgcgt gcgggatgtt tttgaggcca aggcccggca tggtttctgc   420
ggtatcccaa tcacagacac aggccggatg gggagccgct tggtgggcat catctcctcc   480
agggacattg attttctcaa agaggaggaa catgactgtt tcttggaaga gataatgaca   540
aagagggaag acttggtggt agcccctgca ggcatcacac tgaaggaggc aaatgaaatt   600
ctgcagcgca gcaagaaggg aaagttgccc attgtaaatg aagatgatga gcttgtggcc   660
atcattgccc ggacagacct gaagaagaat cgggactacc cactagcctc caaagatgcc   720
aagaaacagc tgctgtgtgg ggcagccatt ggcactcatg aggatgacaa gtataggctg   780
gacttgctcg cccaggctgg tgtggatgta gtggttttgg actcttccca gggaaattcc   840
atcttccaga tcaatatgat caagtacatc aaagacaaat accctaatct ccaagtcatt   900
ggaggcaatg tggtcactgc tgcccaggcc aagaacctca ttgatgcagg tgtggatgcc   960
ctgcgggtgg gcatgggaag tggctccatc tgcattacgc aggaagtgct ggcctgtggg  1020
cggccccaag caacagcagt gtacaaggtg tcagagtatg cacggcgctt tggtgttccg  1080
gtcattgctg atggaggaat ccaaaatgtg gtcatattgc gaaagccttt ggcccttggg  1140
gcctccacag tcatgatggg ctctctcctg gctgccacca ctgaggcccc tggtgaatac  1200
ttcttttccg atgggatccg gctaaagaaa tatcgcggta tgggttctct cgatgccatg  1260
gacaagcacc tcagcagcca gaacagatat ttcagtgaag ctgacaaaat caaagtggcc  1320
cagggagtgt ctggtgctgt gcaggacaaa gggtcaatcc acaaatttgt cccttacctg  1380
attgctggca tccaacactc atgccaggac attggtgcca agagcttgac ccaagtccga  1440
gccatgatgt actctgggga gcttaagttt gagaagagaa cgtcctcagc ccaggtggaa  1500
ggtggcgtcc atagcctcca ttcgtatgag aagcggcttt tctga                  1545
```

Figure 4

```
Met Ala Asp Tyr Leu Ile Ser Gly Gly Thr Ser Tyr Val Pro Asp Asp
1               5                   10                  15

Gly Leu Thr Ala Gln Gln Leu Phe Asn Cys Gly Asp Gly Leu Thr Tyr
            20                  25                  30

Asn Asp Phe Leu Ile Leu Pro Gly Tyr Ile Asp Phe Thr Ala Asp Gln
            35                  40                  45

Val Asp Leu Thr Ser Ala Leu Thr Lys Lys Ile Thr Leu Lys Thr Pro
            50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
            85                  90                  95

Pro Glu Phe Gln Ala Asn Glu Val Arg Lys Val Lys Lys Tyr Glu Gln
            100                 105                 110

Gly Phe Ile Thr Asp Pro Val Val Leu Ser Pro Lys Asp Arg Val Arg
            115                 120                 125

Asp Val Phe Glu Ala Lys Ala Arg His Gly Phe Cys Gly Ile Pro Ile
            130                 135                 140

Thr Asp Thr Gly Arg Met Gly Ser Arg Leu Val Gly Ile Ile Ser Ser
145                 150                 155                 160

Arg Asp Ile Asp Phe Leu Lys Glu Glu Glu His Asp Cys Phe Leu Glu
            165                 170                 175

Glu Ile Met Thr Lys Arg Glu Asp Leu Val Val Ala Pro Ala Gly Ile
            180                 185                 190

Thr Leu Lys Glu Ala Asn Glu Ile Leu Gln Arg Ser Lys Lys Gly Lys
            195                 200                 205

Leu Pro Ile Val Asn Glu Asp Asp Glu Leu Val Ala Ile Ile Ala Arg
            210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
            245                 250                 255

Lys Tyr Arg Leu Asp Leu Leu Ala Gln Ala Gly Val Asp Val Val Val
            260                 265                 270

Leu Asp Ser Ser Gln Gly Asn Ser Ile Phe Gln Ile Asn Met Ile Lys
            275                 280                 285

Tyr Ile Lys Asp Lys Tyr Pro Asn Leu Gln Val Ile Gly Gly Asn Val
            290                 295                 300
```

Figure 5A

```
Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
            325                 330                 335

Leu Ala Cys Gly Arg Pro Gln Ala Thr Ala Val Tyr Lys Val Ser Glu
            340                 345                 350

Tyr Ala Arg Arg Phe Gly Val Pro Val Ile Ala Asp Gly Gly Ile Gln
        355                 360                 365

Asn Val Gly His Ile Ala Lys Ala Leu Ala Leu Gly Ala Ser Thr Val
        370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
            405                 410                 415

Leu Asp Ala Met Asp Lys His Leu Ser Ser Gln Asn Arg Tyr Phe Ser
            420                 425                 430

Glu Ala Asp Lys Ile Lys Val Ala Gln Gly Val Ser Gly Ala Val Gln
        435                 440                 445

Asp Lys Gly Ser Ile His Lys Phe Val Pro Tyr Leu Ile Ala Gly Ile
    450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
            485                 490                 495

Ala Gln Val Glu Gly Gly Val His Ser Leu His Ser Tyr Glu Lys Arg
            500                 505                 510

Leu Phe
```

Figure 5B

```
atgcatcacc atcaccatca cgccgactac ctgattagtg ggggcacgtc ctacgtgcca    60
gacgacggac tcacagcaca gcagctcttc aactgcggag acggcctcac ctacaatgac   120
tttctcattc tccctgggta catcgacttc actgcagacc aggtggacct gacttctgct   180
ctgaccaaga aaatcactct taagacccca ctggtttcct ctcccatgga cacagtcaca   240
gaggctggga tggccatagc aatggcgctt acaggcggta ttggcttcat ccaccacaac   300
tgtacacctg aattccaggc caatgaagtt cggaaagtga agaaatatga cagggattc    360
atcacagacc ctgtggtcct cagccccaag gatcgcgtgc gggatgtttt tgaggccaag   420
gcccggcatg gtttctgcgg tatcccaatc acagacacag gccggatggg gagccgcttg   480
gtgggcatca tctcctccag ggacattgat tttctcaaag aggaggaaca tgactgtttc   540
ttggaagaga taatgacaaa gagggaagac ttggtggtag cccctgcagg catcacactg   600
aaggaggcaa atgaaattct gcagcgcagc aagaagggaa agttgcccat tgtaaatgaa   660
gatgatgagc ttgtggccat cattgcccgg acagacctga agaagaatcg ggactaccca   720
ctagcctcca aagatgccaa gaaacagctg ctgtgtgggg cagccattgg cactcatgag   780
gatgacaagt ataggctgga cttgctcgcc caggctggtg tggatgtagt ggttttggac   840
tcttcccagg gaaattccat cttccagatc aatatgatca agtacatcaa agacaaatac   900
cctaatctcc aagtcattgg aggcaatgtg gtcactgctg cccaggccaa gaacctcatt   960
gatgcaggtg tggatgccct gcgggtgggc atgggaagtg gctccatctg cattacgcag  1020
gaagtgctgg cctgtgggcg gccccaagca acagcagtgt acaaggtgtc agagtatgca  1080
cggcgctttg gtgttccggt cattgctgat ggaggaatcc aaaatgtggg tcatattgcg  1140
aaagccttgg cccttggggc ctccacagtc atgatgggct ctctcctggc tgccaccact  1200
gaggcccctg gtgaatactt ctttccgat gggatccggc taaagaaata tcgcggtatg  1260
ggttctctcg atgccatgga caagcacctc agcagccaga acagatattt cagtgaagct  1320
gacaaaatca agtggccca gggagtgtct ggtgctgtgc aggacaaagg gtcaatccac  1380
aaatttgtcc cttacctgat tgctggcatc caacactcat gccaggacat tggtgccaag  1440
agcttgaccc aagtccgagc catgatgtac tctggggagc ttaagtttga aagagaacg   1500
tcctcagccc aggtggaagg tggcgtccat agcctccatt cgtatgagaa gcggcttttc  1560
tga                                                                1563
```

Figure 6

Met His His His His His Ala Asp Tyr Leu Ile Ser Gly Gly Thr
1       5               10              15

Ser Tyr Val Pro Asp Asp Gly Leu Thr Ala Gln Gln Leu Phe Asn Cys
            20              25              30

Gly Asp Gly Leu Thr Tyr Asn Asp Phe Leu Ile Leu Pro Gly Tyr Ile
        35              40              45

Asp Phe Thr Ala Asp Gln Val Asp Leu Thr Ser Ala Leu Thr Lys Lys
    50              55              60

Ile Thr Leu Lys Thr Pro Leu Val Ser Ser Pro Met Asp Thr Val Thr
65              70              75              80

Glu Ala Gly Met Ala Ile Ala Met Ala Leu Thr Gly Gly Ile Gly Phe
            85              90              95

Ile His His Asn Cys Thr Pro Glu Phe Gln Ala Asn Glu Val Arg Lys
        100             105             110

Val Lys Lys Tyr Glu Gln Gly Phe Ile Thr Asp Pro Val Val Leu Ser
        115             120             125

Pro Lys Asp Arg Val Arg Asp Val Phe Glu Ala Lys Ala Arg His Gly
    130             135             140

Phe Cys Gly Ile Pro Ile Thr Asp Thr Gly Arg Met Gly Ser Arg Leu
145             150             155             160

Val Gly Ile Ile Ser Ser Arg Asp Ile Asp Phe Leu Lys Glu Glu Glu
            165             170             175

His Asp Cys Phe Leu Glu Glu Ile Met Thr Lys Arg Glu Asp Leu Val
            180             185             190

Val Ala Pro Ala Gly Ile Thr Leu Lys Glu Ala Asn Glu Ile Leu Gln
        195             200             205

Arg Ser Lys Lys Gly Lys Leu Pro Ile Val Asn Glu Asp Asp Glu Leu
    210             215             220

Val Ala Ile Ile Ala Arg Thr Asp Leu Lys Lys Asn Arg Asp Tyr Pro
225             230             235             240

Leu Ala Ser Lys Asp Ala Lys Lys Gln Leu Leu Cys Gly Ala Ala Ile
            245             250             255

Gly Thr His Glu Asp Asp Lys Tyr Arg Leu Asp Leu Leu Ala Gln Ala
            260             265             270

Gly Val Asp Val Val Leu Asp Ser Ser Gln Gly Asn Ser Ile Phe
        275             280             285

Gln Ile Asn Met Ile Lys Tyr Ile Lys Asp Lys Tyr Pro Asn Leu Gln
    290             295             300

Val Ile Gly Gly Asn Val Val Thr Ala Ala Gln Ala Lys Asn Leu Ile
305             310             315             320

Figure 7A

```
Asp Ala Gly Val Asp Ala Leu Arg Val Gly Met Gly Ser Gly Ser Ile
            325                 330                 335

Cys Ile Thr Gln Glu Val Leu Ala Cys Gly Arg Pro Gln Ala Thr Ala
            340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
            370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
            405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
            435                 440                 445

Val Ser Gly Ala Val Gln Asp Lys Gly Ser Ile His Lys Phe Val Pro
            450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Gly Val His Ser Leu
            500                 505                 510

His Ser Tyr Glu Lys Arg Leu Phe
            515                 520
```

Figure 7B

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc tccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga cagggattc     360
atcacagacc ctgtggtcct cagccccaag gatcgcgtgc gggatgtttt tgaggccaag     420
gcccggcatg gtttctgcgg tatcccaatc acagacacag gcgaaatggg aagcgagttg     480
gtgggcatca tctcctccag ggacattgat tttctcaaag aggaggaaca tgactgtttc     540
ttggaagaga taatgacaaa gagggaagac ttggtggtag cccctgcagg catcacactg     600
aaggaggcaa atgaaattct gcagcgcagc aagaagggaa agttgcccat tgtaaatgaa     660
gatgatgagc ttgtggccat cattgcccgg acagacctga gaagaatcg ggactaccca      720
ctagcctcca agatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
cggcgctttg gtgttccggt cattgctgat ggaggaatcc aaaatgtggg tcatattgcg    1140
aaagccttgg cccttggggc ctccacagtc atgatgggct ctctcctggc tgccaccact    1200
gaggcccctg gtgaatactt cttttccgat gggatccggc taaagaaata tcgcggtatg    1260
ggttctctcg atgccatgga caagcacctc agcagccaga acagatattt cagtgaagct    1320
gacaaaatca aagtggccca gggagtgtct ggtgctgtgc aggacaaagg gtcaatccac    1380
aaatttgtcc cttacctgat tgctggcatc caacactcat gccaggacat tggtgccaag    1440
agcttgaccc aagtccgagc catgatgtac tctggggagc ttaagtttga aagagaacg     1500
tcctcagccc aggtggaagg tggcgtccat agcctccatt cgtatgagaa gcggcttttc    1560
tga                                                                   1563
```

Figure 8

Met His His His His His Ala Asp Tyr Leu Ile Ser Gly Gly Thr
1       5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
            35                  40                  45

Asp Phe Thr Ala Asp Gln Val Asp Leu Thr Ser Ala Leu Thr Lys Lys
            50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
                85                  90                  95

Ile His His Asn Cys Thr Pro Glu Phe Gln Ala Asn Glu Val Arg Lys
                100                 105                 110

Val Lys Lys Tyr Glu Gln Gly Phe Ile Thr Asp Pro Val Val Leu Ser
            115                 120                 125

Pro Lys Asp Arg Val Arg Asp Val Phe Glu Ala Lys Ala Arg His Gly
        130                 135                 140

Phe Cys Gly Ile Pro Ile Thr Asp Thr Gly Glu Met Gly Ser Glu Leu
145                 150                 155                 160

Val Gly Ile Ile Ser Ser Arg Asp Ile Asp Phe Leu Lys Glu Glu Glu
                165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
        195                 200                 205

Arg Ser Lys Lys Gly Lys Leu Pro Ile Val Asn Glu Asp Asp Glu Leu
        210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
            245                 250                 255

Gly Thr His Glu Asp Asp Lys Tyr Arg Leu Asp Leu Leu Ala Gln Ala
            260                 265                 270

Gly Val Asp Val Val Val Leu Asp Ser Ser Gln Gly Asn Ser Ile Phe
        275                 280                 285

Gln Ile Asn Met Ile Lys Tyr Ile Lys Asp Lys Tyr Pro Asn Leu Gln
            290                 295                 300

Figure 9A

```
Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
                340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
            370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
        435                 440                 445

Val Ser Gly Ala Val Gln Asp Lys Gly Ser Ile His Lys Phe Val Pro
    450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
                485                 490                 495

Glu Lys Arg Thr Ser Ser Ala Gln Val Glu Gly Gly Val His Ser Leu
            500                 505                 510

His Ser Tyr Glu Lys Arg Leu Phe
    515                 520
```

Figure 9B

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc tccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga cagggattc     360
atcacagacc ctgtggtcct cagccccaag gatcgcgtgc gggatgtttt tgaggccaag     420
gcccggcatg gtttctgcgg tatcccaatc acagacacag gccggatggg gagccgcttg     480
gtgggcatca tctcctccga agacattgat tttctcgagg aggaggaaca tgactgtttc     540
ttggaagaga taatgacaaa gagggaagac ttggtggtag ccctgcagg catcacactg      600
aaggaggcaa atgaaattct gcagcgcagc aagaagggaa agttgcccat tgtaaatgaa     660
gatgatgagc ttgtggccat cattgcccgg acagacctga agaagaatcg ggactaccca     720
ctagcctcca agatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
cggcgctttg gtgttccggt cattgctgat ggaggaatcc aaaatgtggg acatattgcg    1140
aaagccttgg ccctctgggc ctccacagac atgatgggct ctctcctggc tgccaccact    1200
gaggcccctg gtgaatactt cttttccgat gggatccggc taaagaaata tcgcggtatg    1260
ggttctctcg atgccatgga caagcacctc agcagccaga acagatattt cagtgaagct    1320
gacaaaatca agtggcccca gggagtgtct ggtgctgtgc aggacaaagg gtcaatccac    1380
aaatttgtcc cttacctgat tgctggcatc caacactcat gccaggacat tggtgccaag    1440
agcttgaccc aagtccgagc catgatgtac tctggggagc ttaagtttga agagaacg     1500
tcctcagccc aggtggaagg tggcgtccat agcctccatt cgtatgagaa gcggctttc    1560
tga                                                                 1563
```

Figure 10

| | | | | | | | | | | | | | |
|---|---|---|---|---|---|---|---|---|---|---|---|---|---|
| Met<br>1 | *His* | *His* | *His*<br>5 | *His* | *His* | Ala | Asp | Tyr<br>10 | Leu | Ile | Ser | Gly | Gly<br>15 | Thr |

Met *His* *His* *His* *His* *His* Ala Asp Tyr Leu Ile Ser Gly Gly Thr
1           5                    10                15

Ser Tyr Val Pro Asp Asp Gly Leu Thr Ala Gln Gln Leu Phe Asn Cys
        20              25              30

Gly Asp Gly Leu Thr Tyr Asn Asp Phe Leu Ile Leu Pro Gly Tyr Ile
        35              40              45

Asp Phe Thr Ala Asp Gln Val Asp Leu Thr Ser Ala Leu Thr Lys Lys
    50              55              60

Ile Thr Leu Lys Thr Pro Leu Val Ser Ser Pro Met Asp Thr Val Thr
65              70              75              80

Glu Ala Gly Met Ala Ile Ala Met Ala Leu Thr Gly Gly Ile Gly Phe
            85              90              95

Ile His His Asn Cys Thr Pro Glu Phe Gln Ala Asn Glu Val Arg Lys
            100             105             110

Val Lys Lys Tyr Glu Gln Gly Phe Ile Thr Asp Pro Val Val Leu Ser
        115             120             125

Pro Lys Asp Arg Val Arg Asp Val Phe Glu Ala Lys Ala Arg His Gly
    130             135             140

Phe Cys Gly Ile Pro Ile Thr Asp Thr Gly Arg Met Gly Ser Arg Leu
145             150             155             160

Val Gly Ile Ile Ser Ser *Glu* Asp Ile Asp Phe Leu *Glu* Glu Glu Glu
            165             170             175

His Asp Cys Phe Leu Glu Glu Ile Met Thr Lys Arg Glu Asp Leu Val
        180             185             190

Val Ala Pro Ala Gly Ile Thr Leu Lys Glu Ala Asn Glu Ile Leu Gln
        195             200             205

Arg Ser Lys Lys Gly Lys Leu Pro Ile Val Asn Glu Asp Asp Glu Leu
        210             215             220

Val Ala Ile Ile Ala Arg Thr Asp Leu Lys Lys Asn Arg Asp Tyr Pro
225             230             235             240

Leu Ala Ser Lys Asp Ala Lys Lys Gln Leu Leu Cys Gly Ala Ala Ile
            245             250             255

Gly Thr His Glu Asp Asp Lys Tyr Arg Leu Asp Leu Leu Ala Gln Ala
        260             265             270

Gly Val Asp Val Val Val Leu Asp Ser Ser Gln Gly Asn Ser Ile Phe
        275             280             285

Gln Ile Asn Met Ile Lys Tyr Ile Lys Asp Lys Tyr Pro Asn Leu Gln
    290             295             300

Figure 11A

```
Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
                340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
        370                 375                 380

Leu Gly Ala Ser Thr Asp Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
                420                 425                 430

Gln Asn Arg Tyr Phe Ser Glu Ala Asp Lys Ile Lys Val Ala Gln Gly
            435                 440                 445

Val Ser Gly Ala Val Gln Asp Lys Gly Ser Ile His Lys Phe Val Pro
        450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
                485                 490                 495

Glu Lys Arg Thr Ser Ser Ala Gln Val Glu Gly Gly Val His Ser Leu
            500                 505                 510

His Ser Tyr Glu Lys Arg Leu Phe
        515                 520
```

Figure 11B

```
atgcatcacc atcaccatca cgccgactac ctgattagtg ggggcacgtc ctacgtgcca    60
gacgacggac tcacagcaca gcagctcttc aactgcggag acggcctcac ctacaatgac   120
tttctcattc tccctgggta catcgacttc actgcagacc aggtggacct gacttctgct   180
ctgaccaaga aaatcactct taagacccca ctggtttcct ctcccatgga cacagtcaca   240
gaggctggga tggccatagc aatggcgctt acaggcggta ttggcttcat ccaccacaac   300
tgtacacctg aattccaggc caatgaagtt cggaaagtga agaaatatga cagggattc   360
atcacagacc ctgtggtcct cagccccaag gatcgcgtgc gggatgtttt tgaggccgaa   420
gccgagcatg gtttctgcgg tatcccaatc acagacacag gccggatggg gagccgcttg   480
gtgggcatca tctcctccag ggacattgat tttctcaaag aggaggaaca tgactgtttc   540
ttggaagaga taatgacaaa gagggaagac ttggtggtag ccctgcagg catcacactg   600
aaggaggcaa atgaaattct gcagcgcagc aagaagggaa agttgcccat tgtaaatgaa   660
gatgatgagc ttgtggccat cattgcccgg acagacctga agaagaatcg ggactaccca   720
ctagcctcca agatgccaa gaaacagctg ctgtgtgggg cagccattgg cactcatgag   780
gatgacaagt ataggctgga cttgctcgcc caggctggtg tggatgtagt ggttttggac   840
tcttcccagg gaaattccat cttccagatc aatatgatca agtacatcaa agacaaatac   900
cctaatctcc aagtcattgg aggcaatgtg gtcactgctg cccaggccaa gaacctcatt   960
gatgcaggtg tggatgccct gcgggtgggc atgggaagtg gctccatctg cattacgcag  1020
gaagtgctgg cctgtgggcg gccccaagca acagcagtgt acaaggtgtc agagtatgca  1080
cggcgctttg gtgttccggt cattgctgat ggaggaatcc aaaatgtggg tcatattgcg  1140
aaagccttgg cccttggggc ctccacagtc atgatgggct ctctcctggc tgccaccact  1200
gaggcccctg gtgaatactt cttttccgat gggatccggc taaagaaata tcgcggtatg  1260
ggttctctcg atgccatgga caagcacctc agcagccaga acagatattt cagtgaagct  1320
gacaaaatca aagtggccca gggagtgtct ggtgctgtgc aggacaaagg gtcaatccac  1380
aaatttgtcc cttacctgat tgctggcatc caacactcat gccaggacat tggtgccaag  1440
agcttgaccc aagtccgagc catgatgtac tctggggagc ttaagtttga gaagagaacg  1500
tcctcagccc aggtggaagg tggcgtccat agcctccatt cgtatgagaa gcggctttc   1560
tga                                                                1563
```

Figure 12

| | | | | | | | | | | | | | | |
|---|---|---|---|---|---|---|---|---|---|---|---|---|---|---|

Met His His His His His Ala Asp Tyr Leu Ile Ser Gly Gly Thr
1          5                    10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
        35                  40                  45

Asp Phe Thr Ala Asp Gln Val Asp Leu Thr Ser Ala Leu Thr Lys Lys
    50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
                85                  90                  95

Ile His His Asn Cys Thr Pro Glu Phe Gln Ala Asn Glu Val Arg Lys
                100                 105                 110

Val Lys Lys Tyr Glu Gln Gly Phe Ile Thr Asp Pro Val Val Leu Ser
        115                 120                 125

Pro Lys Asp Arg Val Arg Asp Val Phe Glu Ala Glu Ala Glu His Gly
    130                 135                 140

Phe Cys Gly Ile Pro Ile Thr Asp Thr Gly Arg Met Gly Ser Arg Leu
145                 150                 155                 160

Val Gly Ile Ile Ser Ser Arg Asp Ile Asp Phe Leu Lys Glu Glu Glu
                165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
        195                 200                 205

Arg Ser Lys Lys Gly Lys Leu Pro Ile Val Asn Glu Asp Asp Glu Leu
    210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
            245                 250                 255

Gly Thr His Glu Asp Asp Lys Tyr Arg Leu Asp Leu Leu Ala Gln Ala
        260                 265                 270

Gly Val Asp Val Val Leu Asp Ser Ser Gln Gly Asn Ser Ile Phe
    275                 280                 285

Gln Ile Asn Met Ile Lys Tyr Ile Lys Asp Lys Tyr Pro Asn Leu Gln
    290                 295                 300

Figure 13A

```
Val Ile Gly Gly Asn Val Val Thr Ala Ala Gln Ala Lys Asn Leu Ile
305             310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
            340                 345                 350

Val Tyr Lys Val Ser Glu Tyr Ala Arg Arg Phe Gly Val Pro Val Ile
        355                 360                 365

Ala Asp Gly Gly Ile Gln Asn Val Gly His Ile Ala Lys Ala Leu Ala
    370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
            405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
        435                 440                 445

Val Ser Gly Ala Val Gln Asp Lys Gly Ser Ile His Lys Phe Val Pro
    450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Gly Val His Ser Leu
            500                 505                 510

His Ser Tyr Glu Lys Arg Leu Phe
            515             520
```

Figure 13B

```
atgcatcacc atcaccatca cgccgactac ctgattagtg ggggcacgtc ctacgtgcca    60
gacgacggac tcacagcaca gcagctcttc aactgcggag acggcctcac ctacaatgac   120
tttctcattc tccctgggta catcgacttc actgcagacc aggtggacct gacttctgct   180
ctgaccaaga aaatcactct taagacccca ctggtttcct ctcccatgga cacagtcaca   240
gaggctggga tggccatagc aatggcgctt acaggcggta ttggcttcat ccaccacaac   300
tgtacacctg aattccaggc caatgaagtt cggaaagtga agaaatatga cagggattc    360
atcacagacc ctgtggtcct cagccccaag gatcgcgtgc gggatgtttt tgaggccaag   420
gcccggcatg gtttctgcgg tatcccaatc acagacacag gccggatggg gagccgcttg   480
gtgggcatca tctcctccga agacattgat tttctcgagg aggaggaaca tgactgtttc   540
ttggaagaga taatgacaaa gagggaagac ttggtggtag cccctgcagg catcacactg   600
aaggaggcaa atgaaattct gcagcgcagc aagaagggaa agttgcccat tgtaaatgaa   660
gatgatgagc ttgtggccat cattgcccgg acagacctga agaagaatcg ggactaccca   720
ctagcctcca agatgccaa gaaacagctg ctgtgtgggg cagccattgg cactcatgag   780
gatgacaagt ataggctgga cttgctcgcc caggctggtg tggatgtagt ggttttggac   840
tcttcccagg gaaattccat cttccagatc aatatgatca agtacatcaa agacaaatac   900
cctaatctcc aagtcattgg aggcaatgtg gtcactgctg cccaggccaa gaacctcatt   960
gatgcaggtg tggatgccct gcgggtgggc atgggaagtg gctccatctg cattacgcag  1020
gaagtgctgg cctgtgggcg gccccaagca acagcagtgt acaaggtgtc agagtatgca  1080
cggcgctttg gtgttccggt cattgctgat ggaggaatcc aaaatgtggg tcatattgcg  1140
aaagccttgg cccttggggc ctccacagtc atgatgggct ctctcctggc tgccaccact  1200
gaggcccctg gtgaatactt cttttccgat gggatccggc taaagaaata tcgcggtatg  1260
ggttctctcg atgccatgga caagcacctc agcagccaga acagatattt cagtgaagct  1320
gacaaaatca agtggccca gggagtgtct ggtgctgtgc aggacaaagg gtcaatccac  1380
aaatttgtcc cttacctgat tgctggcatc caacactcat gccaggacat tggtgccaag  1440
agcttgaccc aagtccgagc catgatgtac tctggggagc ttaagtttga aagagaacg   1500
tcctcagccc aggtggaagg tggcgtccat agcctccatt cgtatgagaa gcggctttc   1560
tga                                                                1563
```

Figure 14

Met His His His His His Ala Asp Tyr Leu Ile Ser Gly Gly Thr
1       5               10              15

Ser Tyr Val Pro Asp Asp Gly Leu Thr Ala Gln Gln Leu Phe Asn Cys
            20              25              30

Gly Asp Gly Leu Thr Tyr Asn Asp Phe Leu Ile Leu Pro Gly Tyr Ile
        35              40              45

Asp Phe Thr Ala Asp Gln Val Asp Leu Thr Ser Ala Leu Thr Lys Lys
        50              55              60

Ile Thr Leu Lys Thr Pro Leu Val Ser Ser Pro Met Asp Thr Val Thr
65              70              75              80

Glu Ala Gly Met Ala Ile Ala Met Ala Leu Thr Gly Gly Ile Gly Phe
            85              90              95

Ile His His Asn Cys Thr Pro Glu Phe Gln Ala Asn Glu Val Arg Lys
            100             105             110

Val Lys Lys Tyr Glu Gln Gly Phe Ile Thr Asp Pro Val Val Leu Ser
        115             120             125

Pro Lys Asp Arg Val Arg Asp Val Phe Glu Ala Lys Ala Arg His Gly
    130             135             140

Phe Cys Gly Ile Pro Ile Thr Asp Thr Gly Arg Met Gly Ser Arg Leu
145             150             155             160

Val Gly Ile Ile Ser Ser Glu Asp Ile Asp Phe Leu Glu Glu Glu Glu
                165             170             175

His Asp Cys Phe Leu Glu Glu Ile Met Thr Lys Arg Glu Asp Leu Val
            180             185             190

Val Ala Pro Ala Gly Ile Thr Leu Lys Glu Ala Asn Glu Ile Leu Gln
            195             200             205

Arg Ser Lys Lys Gly Lys Leu Pro Ile Val Asn Glu Asp Asp Glu Leu
    210             215             220

Val Ala Ile Ile Ala Arg Thr Asp Leu Lys Lys Asn Arg Asp Tyr Pro
225             230             235             240

Leu Ala Ser Lys Asp Ala Lys Lys Gln Leu Leu Cys Gly Ala Ala Ile
            245             250             255

Gly Thr His Glu Asp Asp Lys Tyr Arg Leu Asp Leu Leu Ala Gln Ala
            260             265             270

Gly Val Asp Val Val Leu Asp Ser Ser Gln Gly Asn Ser Ile Phe
            275             280             285

Gln Ile Asn Met Ile Lys Tyr Ile Lys Asp Lys Tyr Pro Asn Leu Gln
            290             295             300

Figure 15A

```
Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
                340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
    370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
        435                 440                 445

Val Ser Gly Ala Val Gln Asp Lys Gly Ser Ile His Lys Phe Val Pro
    450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
                485                 490                 495

Glu Lys Arg Thr Ser Ser Ala Gln Val Glu Gly Gly Val His Ser Leu
            500                 505                 510

His Ser Tyr Glu Lys Arg Leu Phe
        515                 520
```

Figure 15B

```
atgcatcacc atcaccatca cgccgactac ctgattagtg ggggcacgtc ctacgtgcca    60
gacgacggac tcacagcaca gcagctcttc aactgcggag acggcctcac ctacaatgac   120
tttctcattc tccctgggta catcgacttc actgcagacc aggtggacct gacttctgct   180
ctgaccaaga aaatcactct taagacccca ctggtttcct ctcccatgga cacagtcaca   240
gaggctggga tggccatagc aatggcgctt acaggcggta ttggcttcat ccaccacaac   300
tgtacacctg aattccaggc caatgaagtt cggaaagtga agaaatatga cagggattc   360
atcacagacc ctgtggtcct cagccccgaa gatgaggtgg aagatgtttt tgaggccgaa   420
gccgagcatg gtttctgcgg tatcccaatc acagacacag gcgaaatggg aagcgagttg   480
gtgggcatca tctcctccag ggacattgat tttctcaaag aggaggaaca tgactgtttc   540
ttggaagaga taatgacaaa gagggaagac ttggtggtag cccctgcagg catcacactg   600
aaggaggcaa atgaaattct gcagcgcagc aagaagggaa agttgcccat tgtaaatgaa   660
gatgatgagc ttgtggccat cattgcccgg acagacctga gaagaatcg ggactaccca   720
ctagcctcca aagatgccaa gaaacagctg ctgtgtgggg cagccattgg cactcatgag   780
gatgacaagt ataggctgga cttgctcgcc caggctggtg tggatgtagt ggttttggac   840
tcttcccagg gaaattccat cttccagatc aatatgatca agtacatcaa agacaaatac   900
cctaatctcc aagtcattgg aggcaatgtg gtcactgctg cccaggccaa gaacctcatt   960
gatgcaggtg tggatgccct gcgggtgggc atgggaagtg ctccatctg cattacgcag  1020
gaagtgctgg cctgtgggcg gccccaagca acagcagtgt acaaggtgtc agagtatgca  1080
cggcgctttg gtgttccggt cattgctgat ggaggaatcc aaaatgtggg tcatattgcg  1140
aaagccttgg cccttggggc ctccacagtc atgatgggct ctctcctggc tgccaccact  1200
gaggcccctg gtgaatactt cttttccgat gggatccggc taaagaaata tcgcggtatg  1260
ggttctctcg atgccatgga caagcacctc agcagccaga acagatattt cagtgaagct  1320
gacaaaatca agtggccca gggagtgtct ggtgctgtgc aggacaaagg tcaatccac  1380
aaatttgtcc cttacctgat tgctggcatc caacactcat gccaggacat tggtgccaag  1440
agcttgaccc aagtccgagc catgatgtac tctggggagc ttaagtttga aagagaacg  1500
tcctcagccc aggtggaagg tggcgtccat agcctccatt cgtatgagaa gcggcttttc  1560
tga                                                                1563
```

Figure 16

Met His His His His His Ala Asp Tyr Leu Ile Ser Gly Gly Thr
1       5               10              15

Ser Tyr Val Pro Asp Asp Gly Leu Thr Ala Gln Gln Leu Phe Asn Cys
            20              25              30

Gly Asp Gly Leu Thr Tyr Asn Asp Phe Leu Ile Leu Pro Gly Tyr Ile
        35              40              45

Asp Phe Thr Ala Asp Gln Val Asp Leu Thr Ser Ala Leu Thr Lys Lys
    50              55              60

Ile Thr Leu Lys Thr Pro Leu Val Ser Ser Pro Met Asp Thr Val Thr
65              70              75              80

Glu Ala Gly Met Ala Ile Ala Met Ala Leu Thr Gly Gly Ile Gly Phe
            85              90              95

Ile His His Asn Cys Thr Pro Glu Phe Gln Ala Asn Glu Val Arg Lys
        100             105             110

Val Lys Lys Tyr Glu Gln Gly Phe Ile Thr Asp Pro Val Val Leu Ser
        115             120             125

Pro Glu Asp Glu Val Glu Asp Val Phe Glu Ala Glu Ala Glu His Gly
    130             135             140

Phe Cys Gly Ile Pro Ile Thr Asp Thr Gly Glu Met Gly Ser Glu Leu
145             150             155             160

Val Gly Ile Ile Ser Ser Arg Asp Ile Asp Phe Leu Lys Glu Glu Glu
            165             170             175

His Asp Cys Phe Leu Glu Glu Ile Met Thr Lys Arg Glu Asp Leu Val
        180             185             190

Val Ala Pro Ala Gly Ile Thr Leu Lys Glu Ala Asn Glu Ile Leu Gln
        195             200             205

Arg Ser Lys Lys Gly Lys Leu Pro Ile Val Asn Glu Asp Asp Glu Leu
    210             215             220

Val Ala Ile Ile Ala Arg Thr Asp Leu Lys Lys Asn Arg Asp Tyr Pro
225             230             235             240

Leu Ala Ser Lys Asp Ala Lys Lys Gln Leu Leu Cys Gly Ala Ala Ile
            245             250             255

Gly Thr His Glu Asp Asp Lys Tyr Arg Leu Asp Leu Leu Ala Gln Ala
        260             265             270

Gly Val Asp Val Val Leu Asp Ser Ser Gln Gly Asn Ser Ile Phe
        275             280             285

Gln Ile Asn Met Ile Lys Tyr Ile Lys Asp Lys Tyr Pro Asn Leu Gln
    290             295             300

Figure 17A

```
Val Ile Gly Gly Asn Val Val Thr Ala Ala Gln Ala Lys Asn Leu Ile
305             310             315                 320

Asp Ala Gly Val Asp Ala Leu Arg Val Gly Met Gly Ser Gly Ser Ile
                325             330             335

Cys Ile Thr Gln Glu Val Leu Ala Cys Gly Arg Pro Gln Ala Thr Ala
            340             345             350

Val Tyr Lys Val Ser Glu Tyr Ala Arg Arg Phe Gly Val Pro Val Ile
        355             360             365

Ala Asp Gly Gly Ile Gln Asn Val Gly His Ile Ala Lys Ala Leu Ala
    370             375             380

Leu Gly Ala Ser Thr Val Met Met Gly Ser Leu Leu Ala Ala Thr Thr
385             390             395                 400

Glu Ala Pro Gly Glu Tyr Phe Phe Ser Asp Gly Ile Arg Leu Lys Lys
            405             410             415

Tyr Arg Gly Met Gly Ser Leu Asp Ala Met Asp Lys His Leu Ser Ser
            420             425             430

Gln Asn Arg Tyr Phe Ser Glu Ala Asp Lys Ile Lys Val Ala Gln Gly
            435             440             445

Val Ser Gly Ala Val Gln Asp Lys Gly Ser Ile His Lys Phe Val Pro
    450             455             460

Tyr Leu Ile Ala Gly Ile Gln His Ser Cys Gln Asp Ile Gly Ala Lys
465             470             475                 480

Ser Leu Thr Gln Val Arg Ala Met Met Tyr Ser Gly Glu Leu Lys Phe
            485             490             495

Glu Lys Arg Thr Ser Ser Ala Gln Val Glu Gly Gly Val His Ser Leu
            500             505             510

His Ser Tyr Glu Lys Arg Leu Phe
            515             520
```

Figure 17B

```
                        SEQUENCE LISTING

<160> NUMBER OF SEQ ID NOS: 22

<210> SEQ ID NO 1
<211> LENGTH: 43
<212> TYPE: DNA
<213> ORGANISM: Homo sapiens

<400> SEQUENCE: 1
ggagatatac atatgcatca ccatcaccat cacgccgact acc                43

<210> SEQ ID NO 2
<211> LENGTH: 43
<212> TYPE: DNA
<213> ORGANISM: Homo sapiens

<400> SEQUENCE: 2
ggtagtcggc gtgatggtga tggtgatgca tatgtatatc tcc                43

<210> SEQ ID NO 3
<211> LENGTH: 64
<212> TYPE: DNA
<213> ORGANISM: Homo sapiens

<400> SEQUENCE: 3
ggtcctcagc cccgaagatg aggtggaaga tgtttttgag gccgaagccg agcatggttt    60
ctgc                                                                64
```

<210> SEQ ID NO 4
<211> LENGTH: 64
<212> TYPE: DNA
<213> ORGANISM: Homo sapiens

<400> SEQUENCE: 4

```
gcagaaacca tgctcggctt cggcctcaaa aacatcttcc acctcatctt cggggctgag    60
gacc                                                                 64
```

<210> SEQ ID NO 5
<211> LENGTH: 39
<212> TYPE: DNA
<213> ORGANISM: Homo sapiens

<400> SEQUENCE: 5

```
ccaatcacag acacaggcga aatggggagc gagttggtg                           39
```

<210> SEQ ID NO 6
<211> LENGTH: 39
<212> TYPE: DNA
<213> ORGANISM: Homo sapiens

<400> SEQUENCE: 6

```
caccaactcg ctcccccattt cgcctgtgtc tgtgattgg                          39
```

<210> SEQ ID NO 7
<211> LENGTH: 46
<212> TYPE: DNA
<213> ORGANISM: Homo sapiens

<400> SEQUENCE: 7

```
ggcatcatct cctccgaaga cattgatttt ctcgaggagg aggaac                   46
```

<210> SEQ ID NO 8
<211> LENGTH: 46
<212> TYPE: DNA
<213> ORGANISM: Homo sapiens

<400> SEQUENCE: 8

```
gttcctcctc ctcgagaaaa tcaatgtctt cggaggagat gatgcc                   46
```

<210> SEQ ID NO 9
<211> LENGTH: 1545
<212> TYPE: DNA
<213> ORGANISM: Homo sapiens
<220> FEATURE:
<221> NAME/KEY: misc_feature
<222> LOCATION: (350)..(555)
<223> OTHER INFORMATION: subdomain

<400> SEQUENCE: 9

```
atggccgact acctgattag tggggggcacg tcctacgtgc cagacgacgg actcacagca    60
cagcagctct tcaactgcgg agacggcctc acctacaatg actttctcat tctccctggg   120
tacatcgact tcactgcaga ccaggtggac ctgacttctg ctctgaccaa gaaaatcact   180
cttaagaccc cactggtttc ctctcccatg gacacagtca cagaggctgg gatggccata   240
gcaatggcgc ttacaggcgg tattggcttc atccaccaca actgtacacc tgaattccag   300
gccaatgaag ttcggaaagt gaagaaatat gaacagggat tcatcacaga ccctgtggtc   360
ctcagcccca aggatcgcgt gcgggatgtt tttgaggcca aggcccggca tggtttctgc   420
```

-continued

| | |
|---|---|
| ggtatcccaa tcacagacac aggccggatg gggagccgct tggtgggcat catctcctcc | 480 |
| agggacattg attttctcaa agaggaggaa catgactgtt tcttggaaga gataatgaca | 540 |
| aagagggaag acttggtggt agcccctgca ggcatcacac tgaaggaggc aaatgaaatt | 600 |
| ctgcagcgca gcaagaaggg aaagttgccc attgtaaatg aagatgatga gcttgtggcc | 660 |
| atcattgccc ggacagacct gaagaagaat cgggactacc cactagcctc caaagatgcc | 720 |
| aagaaacagc tgctgtgtgg ggcagccatt ggcactcatg aggatgacaa gtataggctg | 780 |
| gacttgctcg cccaggctgg tgtggatgta gtggttttgg actcttccca gggaaattcc | 840 |
| atcttccaga tcaatatgat caagtacatc aaagacaaat accctaatct ccaagtcatt | 900 |
| ggaggcaatg tggtcactgc tgcccaggcc aagaacctca ttgatgcagg tgtggatgcc | 960 |
| ctgcgggtgg gcatgggaag tggctccatc tgcattacgc aggaagtgct ggcctgtggg | 1020 |
| cggccccaag caacagcagt gtacaaggtg tcagagtatg cacggcgctt ggtgttccg | 1080 |
| gtcattgctg atgaggaat ccaaaatgtg gtcatattg cgaaagcctt ggcccttggg | 1140 |
| gcctccacag tcatgatggg ctctctcctg gctgccacca ctgaggcccc tggtgaatac | 1200 |
| ttcttttccg atgggatccg gctaaagaaa tatcgcggta tgggttctct cgatgccatg | 1260 |
| gacaagcacc tcagcagcca gaacagatat ttcagtgaag ctgacaaaat caaagtggcc | 1320 |
| cagggagtgt ctggtgctgt gcaggacaaa gggtcaatcc acaaatttgt cccttacctg | 1380 |
| attgctggca tccaacactc atgccaggac attggtgcca agagcttgac ccaagtccga | 1440 |
| gccatgatgt actctgggga gcttaagttt gagaagagaa cgtcctcagc ccaggtggaa | 1500 |
| ggtggcgtcc atagcctcca ttcgtatgag aagcggcttt tctga | 1545 |

<210> SEQ ID NO 10
<211> LENGTH: 514
<212> TYPE: PRT
<213> ORGANISM: Homo sapiens
<220> FEATURE:
<221> NAME/KEY: DOMAIN
<222> LOCATION: (111)..(243)
<223> OTHER INFORMATION: subdomain

<400> SEQUENCE: 10

```
Met Ala Asp Tyr Leu Ile Ser Gly Gly Thr Ser Tyr Val Pro Asp Asp
1               5                  10                  15

Gly Leu Thr Ala Gln Gln Leu Phe Asn Cys Gly Asp Gly Leu Thr Tyr
            20                  25                  30

Asn Asp Phe Leu Ile Leu Pro Gly Tyr Ile Asp Phe Thr Ala Asp Gln
        35                  40                  45

Val Asp Leu Thr Ser Ala Leu Thr Lys Lys Ile Thr Leu Lys Thr Pro
    50                  55                  60

Leu Val Ser Ser Pro Met Asp Thr Val Thr Glu Ala Gly Met Ala Ile
65                  70                  75                  80

Ala Met Ala Leu Thr Gly Gly Ile Gly Phe Ile His His Asn Cys Thr
                85                  90                  95

Pro Glu Phe Gln Ala Asn Glu Val Arg Lys Val Lys Lys Tyr Glu Gln
            100                 105                 110

Gly Phe Ile Thr Asp Pro Val Val Leu Ser Pro Lys Asp Arg Val Arg
        115                 120                 125

Asp Val Phe Glu Ala Lys Ala Arg His Gly Phe Cys Gly Ile Pro Ile
    130                 135                 140

Thr Asp Thr Gly Arg Met Gly Ser Arg Leu Val Gly Ile Ile Ser Ser
145                 150                 155                 160
```

```
Arg Asp Ile Asp Phe Leu Lys Glu Glu His Asp Cys Phe Leu Glu
            165                 170                 175

Glu Ile Met Thr Lys Arg Glu Asp Leu Val Val Ala Pro Ala Gly Ile
        180                 185                 190

Thr Leu Lys Glu Ala Asn Glu Ile Leu Gln Arg Ser Lys Lys Gly Lys
        195                 200                 205

Leu Pro Ile Val Asn Glu Asp Glu Leu Val Ala Ile Ile Ala Arg
    210                 215                 220

Thr Asp Leu Lys Lys Asn Arg Asp Tyr Pro Leu Ala Ser Lys Asp Ala
225                 230                 235                 240

Lys Lys Gln Leu Leu Cys Gly Ala Ala Ile Gly Thr His Glu Asp Asp
            245                 250                 255

Lys Tyr Arg Leu Asp Leu Leu Ala Gln Ala Gly Val Asp Val Val
        260                 265                 270

Leu Asp Ser Ser Gln Gly Asn Ser Ile Phe Gln Ile Asn Met Ile Lys
        275                 280                 285

Tyr Ile Lys Asp Lys Tyr Pro Asn Leu Gln Val Ile Gly Gly Asn Val
    290                 295                 300

Val Thr Ala Ala Gln Ala Lys Asn Leu Ile Asp Ala Gly Val Asp Ala
305                 310                 315                 320

Leu Arg Val Gly Met Gly Ser Gly Ser Ile Cys Ile Thr Gln Glu Val
            325                 330                 335

Leu Ala Cys Gly Arg Pro Gln Ala Thr Ala Val Tyr Lys Val Ser Glu
        340                 345                 350

Tyr Ala Arg Arg Phe Gly Val Pro Val Ile Ala Asp Gly Gly Ile Gln
        355                 360                 365

Asn Val Gly His Ile Ala Lys Ala Leu Ala Leu Gly Ala Ser Thr Val
    370                 375                 380

Met Met Gly Ser Leu Leu Ala Ala Thr Thr Glu Ala Pro Gly Glu Tyr
385                 390                 395                 400

Phe Phe Ser Asp Gly Ile Arg Leu Lys Lys Tyr Arg Gly Met Gly Ser
            405                 410                 415

Leu Asp Ala Met Asp Lys His Leu Ser Ser Gln Asn Arg Tyr Phe Ser
        420                 425                 430

Glu Ala Asp Lys Ile Lys Val Ala Gln Gly Val Ser Gly Ala Val Gln
        435                 440                 445

Asp Lys Gly Ser Ile His Lys Phe Val Pro Tyr Leu Ile Ala Gly Ile
    450                 455                 460

Gln His Ser Cys Gln Asp Ile Gly Ala Lys Ser Leu Thr Gln Val Arg
465                 470                 475                 480

Ala Met Met Tyr Ser Gly Glu Leu Lys Phe Glu Lys Arg Thr Ser Ser
            485                 490                 495

Ala Gln Val Glu Gly Gly Val His Ser Leu His Ser Tyr Glu Lys Arg
        500                 505                 510

Leu Phe

<210> SEQ ID NO 11
<211> LENGTH: 1563
<212> TYPE: DNA
<213> ORGANISM: Homo sapiens
<220> FEATURE:
<221> NAME/KEY: mutation
<222> LOCATION: (4)..(21)
<223> OTHER INFORMATION: insertion
<220> FEATURE:
```

<220> NAME/KEY: misc_feature
<222> LOCATION: (350)..(555)
<223> OTHER INFORMATION: subdomain

<400> SEQUENCE: 11

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc tccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga caggggattc     360
atcacagacc ctgtggtcct cagccccaag gatcgcgtgc gggatgtttt tgaggccaag     420
gcccggcatg gtttctgcgg tatcccaatc acagacacag gccggatggg gagccgcttg     480
gtgggcatca tctcctccag ggacattgat tttctcaaag aggaggaaca tgactgtttc     540
ttggaagaga taatgacaaa gagggaagac ttggtggtag cccctgcagg catcacactg     600
aaggaggcaa atgaaattct gcagcgcagc aagaagggaa agttgcccat tgtaaatgaa     660
gatgatgagc ttgtggccat cattgcccgg acagacctga gaagaatcg ggactaccca      720
ctagcctcca aagatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
cggcgctttg gtgttccggt cattgctgat ggaggaatcc aaaatgtggg tcatattgcg    1140
aaagccttgg cccttggggc ctccacagtc atgatgggct ctctcctggc tgccaccact    1200
gaggcccctg gtgaatactt cttttccgat gggatccggc taaagaaata tcgcggtatg    1260
ggttctctcg atgccatgga caagcacctc agcagccaga acagatattt cagtgaagct    1320
gacaaaatca agtggcccca gggagtgtct ggtgctgtgc aggacaaagg gtcaatccac    1380
aaatttgtcc cttacctgat tgctggcatc caacactcat gccaggacat tggtgccaag    1440
agcttgaccc aagtccgagc catgatgtac tctggggagc ttaagtttga aagagaacg     1500
tcctcagccc aggtggaagg tggcgtccat agcctccatt cgtatgagaa gcggcttttc    1560
tga                                                                  1563
```

<210> SEQ ID NO 12
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag

<400> SEQUENCE: 12

```
Met His His His His His His Ala Asp Tyr Leu Ile Ser Gly Gly Thr
1               5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
```

-continued

```
                35                  40                  45
Asp Phe Thr Ala Asp Gln Val Asp Leu Thr Ser Ala Leu Thr Lys Lys
 50                  55                  60

Ile Thr Leu Lys Thr Pro Leu Val Ser Ser Pro Met Asp Thr Val Thr
 65                  70                  75                  80

Glu Ala Gly Met Ala Ile Ala Met Ala Leu Thr Gly Gly Ile Gly Phe
                 85                  90                  95

Ile His His Asn Cys Thr Pro Glu Phe Gln Ala Asn Glu Val Arg Lys
                100                 105                 110

Val Lys Lys Tyr Glu Gln Gly Phe Ile Thr Asp Pro Val Val Leu Ser
            115                 120                 125

Pro Lys Asp Arg Val Arg Asp Val Phe Glu Ala Lys Ala Arg His Gly
    130                 135                 140

Phe Cys Gly Ile Pro Ile Thr Asp Thr Gly Arg Met Gly Ser Arg Leu
145                 150                 155                 160

Val Gly Ile Ile Ser Ser Arg Asp Ile Asp Phe Leu Lys Glu Glu Glu
                165                 170                 175

His Asp Cys Phe Leu Glu Glu Ile Met Thr Lys Arg Glu Asp Leu Val
                180                 185                 190

Val Ala Pro Ala Gly Ile Thr Leu Lys Glu Ala Asn Glu Ile Leu Gln
            195                 200                 205

Arg Ser Lys Lys Gly Lys Leu Pro Ile Val Asn Glu Asp Asp Glu Leu
    210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
                245                 250                 255

Gly Thr His Glu Asp Asp Lys Tyr Arg Leu Asp Leu Leu Ala Gln Ala
                260                 265                 270

Gly Val Asp Val Val Leu Asp Ser Ser Gln Gly Asn Ser Ile Phe
            275                 280                 285

Gln Ile Asn Met Ile Lys Tyr Ile Lys Asp Lys Tyr Pro Asn Leu Gln
    290                 295                 300

Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
                340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
    370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
                420                 425                 430

Gln Asn Arg Tyr Phe Ser Glu Ala Asp Lys Ile Lys Val Ala Gln Gly
            435                 440                 445

Val Ser Gly Ala Val Gln Asp Lys Gly Ser Ile His Lys Phe Val Pro
    450                 455                 460
```

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Val His Ser Leu
        500                 505                 510

His Ser Tyr Glu Lys Arg Leu Phe
        515                 520

<210> SEQ ID NO 13
<211> LENGTH: 1563
<212> TYPE: DNA
<213> ORGANISM: Homo sapiens
<220> FEATURE:
<221> NAME/KEY: mutation
<222> LOCATION: (4)..(21)
<223> OTHER INFORMATION: insertion
<220> FEATURE:
<221> NAME/KEY: misc_feature
<222> LOCATION: (350)..(555)
<223> OTHER INFORMATION: subdomain

<400> SEQUENCE: 13

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc ccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga acagggattc     360
atcacagacc ctgtggtcct cagccccaag gatcgcgtgc gggatgtttt tgaggccaag     420
gcccggcatg gtttctgcgg tatcccaatc acagacacag cgaaatggga agcgagttg     480
gtgggcatca tctcctccag ggacattgat tttctcaaag aggaggaaca tgactgtttc     540
ttggaagaga taatgacaaa gagggaagac ttggtggtag cccctgcagg catcacactg     600
aaggaggcaa atgaaattct gcagcgcagc aagaagggaa agttgcccat tgtaaatgaa     660
gatgatgagc ttgtggccat cattgcccgg acagacctga gaagaatcg gactaccca     720
ctagcctcca agatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
cggcgctttg gtgttccggt cattgctgat ggaggaatcc aaaatgtggg tcatattgcg    1140
aaagccttgg cccttgggc ctccacagtc atgatgggct ctctcctggc tgccaccact    1200
gaggcccctg gtgaatactt cttttccgat gggatccggc taaagaaata tcgcggtatg    1260
ggttctctcg atgccatgga caagcacctc agcagccaga acagatattt cagtgaagct    1320
gacaaaatca aagtggccca gggagtgtct ggtgctgtgc aggacaaagg gtcaatccac    1380
aaatttgtcc cttacctgat tgctggcatc aacactcat gccaggacat tggtgccaag    1440
agcttgaccc aagtccgagc catgatgtac tctggggagc ttaagtttga aagagaacg    1500
```

```
tcctcagccc aggtggaagg tggcgtccat agcctccatt cgtatgagaa gcggcttttc   1560
tga                                                                 1563
```

<210> SEQ ID NO 14
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag
<220> FEATURE:
<221> NAME/KEY: MISC_FEATURE
<222> LOCATION: (155)..(155)
<223> OTHER INFORMATION: mutation
<220> FEATURE:
<221> NAME/KEY: MISC_FEATURE
<222> LOCATION: (159)..(159)
<223> OTHER INFORMATION: mutation

<400> SEQUENCE: 14

```
Met His His His His His Ala Asp Tyr Leu Ile Ser Gly Gly Thr
1               5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
        35                  40                  45

Asp Phe Thr Ala Asp Gln Val Asp Leu Thr Ser Ala Leu Thr Lys Lys
    50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
                85                  90                  95

Ile His His Asn Cys Thr Pro Glu Phe Gln Ala Asn Glu Val Arg Lys
            100                 105                 110

Val Lys Lys Tyr Glu Gln Gly Phe Ile Thr Asp Pro Val Val Leu Ser
        115                 120                 125

Pro Lys Asp Arg Val Arg Asp Val Phe Glu Ala Lys Ala Arg His Gly
    130                 135                 140

Phe Cys Gly Ile Pro Ile Thr Asp Thr Gly Glu Met Gly Ser Glu Leu
145                 150                 155                 160

Val Gly Ile Ile Ser Ser Arg Asp Ile Asp Phe Leu Lys Glu Glu Glu
                165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
        195                 200                 205

Arg Ser Lys Lys Gly Lys Leu Pro Ile Val Asn Glu Asp Asp Glu Leu
    210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
                245                 250                 255

Gly Thr His Glu Asp Asp Lys Tyr Arg Leu Asp Leu Leu Ala Gln Ala
            260                 265                 270

Gly Val Asp Val Val Val Leu Asp Ser Ser Gln Gly Asn Ser Ile Phe
        275                 280                 285

Gln Ile Asn Met Ile Lys Tyr Ile Lys Asp Lys Tyr Pro Asn Leu Gln
```

```
                290                 295                 300
Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
                325                 330                 335

Cys Ile Thr Gln Glu Val Leu Ala Cys Gly Arg Pro Gln Ala Thr Ala
                340                 345                 350

Val Tyr Lys Val Ser Glu Tyr Ala Arg Arg Phe Gly Val Pro Val Ile
                355                 360                 365

Ala Asp Gly Gly Ile Gln Asn Val Gly His Ile Ala Lys Ala Leu Ala
                370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
                420                 425                 430

Gln Asn Arg Tyr Phe Ser Glu Ala Asp Lys Ile Lys Val Ala Gln Gly
                435                 440                 445

Val Ser Gly Ala Val Gln Asp Lys Gly Ser Ile His Lys Phe Val Pro
                450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
                485                 490                 495

Glu Lys Arg Thr Ser Ser Ala Gln Val Glu Gly Gly Val His Ser Leu
                500                 505                 510

His Ser Tyr Glu Lys Arg Leu Phe
                515                 520
```

<210> SEQ ID NO 15
<211> LENGTH: 1563
<212> TYPE: DNA
<213> ORGANISM: Homo sapiens
<220> FEATURE:
<221> NAME/KEY: mutation
<222> LOCATION: (4)..(21)
<223> OTHER INFORMATION: insertion
<220> FEATURE:
<221> NAME/KEY: misc_feature
<222> LOCATION: (350)..(555)
<223> OTHER INFORMATION: subdomain

<400> SEQUENCE: 15

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc ccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga cagggattc     360 atcacagacc ctgtggtcct cagccccaag gatcgcgtgc gggatgtttt tgaggccaag     420
gcccggcatg gtttctgcgg tatcccaatc acagacacag gccgatggg gagccgcttg     480 gtgggcatca tctcctccga agacattgat tttctcgagg aggaggaaca tgactgtttc     540
ttggaagaga taatgacaaa gagggaagac ttggtggtag cccctgcagg catcacactg     600
```

-continued

```
aaggaggcaa atgaaattct gcagcgcagc aagaagggaa agttgcccat tgtaaatgaa      660
gatgatgagc ttgtggccat cattgcccgg acagacctga agaagaatcg ggactaccca      720
ctagcctcca aagatgccaa gaaacagctg ctgtgtgggg cagccattgg cactcatgag      780
gatgacaagt ataggctgga cttgctcgcc caggctggtg tggatgtagt ggttttggac      840
tcttcccagg gaaattccat cttccagatc aatatgatca agtacatcaa agacaaatac      900
cctaatctcc aagtcattgg aggcaatgtg gtcactgctg cccaggccaa gaacctcatt      960
gatgcaggtg tggatgccct gcgggtgggc atgggaagtg gctccatctg cattacgcag     1020
gaagtgctgg cctgtgggcg gccccaagca acagcagtgt acaaggtgtc agagtatgca     1080
cggcgctttg tgttccggt cattgctgat ggaggaatcc aaaatgtggg acatattgcg      1140
aaagccttgg cccttggggc tccacagac atgatgggct ctctcctggc tgccaccact      1200
gaggcccctg gtgaatactt cttttccgat gggatccggc taaagaaata tcgcggtatg     1260
ggttctctcg atgccatgga caagcacctc agcagccaga acagatattt cagtgaagct     1320
gacaaaatca agtggcccca gggagtgtct ggtgctgtgc aggacaaagg gtcaatccac     1380
aaatttgtcc cttacctgat tgctggcatc caacactcat gccaggacat tggtgccaag     1440
agcttgaccc aagtccgagc catgatgtac tctggggagc ttaagtttga aagagaacg      1500 tcctcagccc aggtggaagg tggcgtccat agcctccatt cgtatgagaa gcggcttttc     1560
tga                                                                  1563
```

<210> SEQ ID NO 16
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag
<220> FEATURE:
<221> NAME/KEY: MISC_FEATURE
<222> LOCATION: (167)..(167)
<223> OTHER INFORMATION: mutation
<220> FEATURE:
<221> NAME/KEY: MISC_FEATURE
<222> LOCATION: (173)..(173)
<223> OTHER INFORMATION: mutation

<400> SEQUENCE: 16

```
Met His His His His His His Ala Asp Tyr Leu Ile Ser Gly Gly Thr
1               5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
        35                  40                  45

Asp Phe Thr Ala Asp Gln Val Asp Leu Thr Ser Ala Leu Thr Lys Lys
    50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
                85                  90                  95

Ile His His Asn Cys Thr Pro Glu Phe Gln Ala Asn Glu Val Arg Lys
            100                 105                 110

Val Lys Lys Tyr Glu Gln Gly Phe Ile Thr Asp Pro Val Val Leu Ser
        115                 120                 125
```

-continued

```
Pro Lys Asp Arg Val Arg Asp Val Phe Glu Ala Lys Ala Arg His Gly
130                 135                 140

Phe Cys Gly Ile Pro Ile Thr Asp Thr Gly Arg Met Gly Ser Arg Leu
145                 150                 155                 160

Val Gly Ile Ile Ser Ser Glu Asp Ile Asp Phe Leu Glu Glu Glu
            165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
            195                 200                 205

Arg Ser Lys Lys Gly Lys Leu Pro Ile Val Asn Glu Asp Asp Glu Leu
210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
            245                 250                 255

Gly Thr His Glu Asp Asp Lys Tyr Arg Leu Asp Leu Leu Ala Gln Ala
            260                 265                 270

Gly Val Asp Val Val Leu Asp Ser Ser Gln Gly Asn Ser Ile Phe
            275                 280                 285

Gln Ile Asn Met Ile Lys Tyr Ile Lys Asp Lys Tyr Pro Asn Leu Gln
290                 295                 300

Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
            325                 330                 335

Cys Ile Thr Gln Glu Val Leu Ala Cys Gly Arg Pro Gln Ala Thr Ala
            340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
370                 375                 380

Leu Gly Ala Ser Thr Asp Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
            405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
            435                 440                 445

Val Ser Gly Ala Val Gln Asp Lys Gly Ser Ile His Lys Phe Val Pro
450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Gly Val His Ser Leu
            500                 505                 510

His Ser Tyr Glu Lys Arg Leu Phe
            515                 520
```

<210> SEQ ID NO 17
<211> LENGTH: 1563
<212> TYPE: DNA

<213> ORGANISM: Homo sapiens
<220> FEATURE:
<221> NAME/KEY: mutation
<222> LOCATION: (4)..(21)
<223> OTHER INFORMATION: insertion
<220> FEATURE:
<221> NAME/KEY: misc_feature
<222> LOCATION: (350)..(555)
<223> OTHER INFORMATION: subdomain

<400> SEQUENCE: 17

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc tccctgggta catcgacttc actgcagacc aggtggacct gacttctgct     180
ctgaccaaga aaatcactct taagacccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga cagggattc     360
atcacagacc ctgtggtcct cagccccaag gatcgcgtgc gggatgtttt tgaggccgaa     420
gccgagcatg ttttctgcgg tatcccaatc acagacacag gccggatggg gagccgcttg     480
gtgggcatca tctcctccag ggacattgat tttctcaaag aggaggaaca tgactgtttc     540
ttggaagaga taatgacaaa gagggaagac ttggtggtag cccctgcagg catcacactg     600
aaggaggcaa atgaaattct gcagcgcagc aagaagggaa agttgcccat tgtaaatgaa     660
gatgatgagc ttgtggccat cattgcccgg acagacctga gaagaatcg ggactaccca      720
ctagcctcca agatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
cggcgctttg gtgttccggt cattgctgat ggaggaatcc aaaatgtggg tcatattgcg    1140
aaagccttgg cccttggggc ctccacagtc atgatgggct ctctcctggc tgccaccact    1200
gaggcccctg gtgaatactt cttttccgat gggatccggc taaagaaata tcgcggtatg    1260
ggttctctcg atgccatgga caagcacctc agcagccaga acagatattt cagtgaagct    1320
gacaaaatca agtggcccca gggagtgtct ggtgctgtgc aggacaaagg gtcaatccac    1380
aaatttgtcc cttacctgat tgctggcatc caacactcat gccaggacat tggtgccaag    1440
agcttgaccc aagtccgagc catgatgtac tctggggagc ttaagtttga aagagaacg     1500
tcctcagccc aggtggaagg tggcgtccat agcctccatt cgtatgagaa gcggcttttc    1560
tga                                                                   1563
```

<210> SEQ ID NO 18
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag
<220> FEATURE:
<221> NAME/KEY: MISC_FEATURE
<222> LOCATION: (140)..(140)
<223> OTHER INFORMATION: mutation

```
<220> FEATURE:
<221> NAME/KEY: MISC_FEATURE
<222> LOCATION: (142)..(142)
<223> OTHER INFORMATION: mutation

<400> SEQUENCE: 18

Met His His His His His Ala Asp Tyr Leu Ile Ser Gly Gly Thr
1               5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
            35                  40                  45

Asp Phe Thr Ala Asp Gln Val Asp Leu Thr Ser Ala Leu Thr Lys Lys
50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
            85                  90                  95

Ile His His Asn Cys Thr Pro Glu Phe Gln Ala Asn Glu Val Arg Lys
            100                 105                 110

Val Lys Lys Tyr Glu Gln Gly Phe Ile Thr Asp Pro Val Val Leu Ser
            115                 120                 125

Pro Lys Asp Arg Val Arg Asp Val Phe Glu Ala Glu Ala Glu His Gly
130                 135                 140

Phe Cys Gly Ile Pro Ile Thr Asp Thr Gly Arg Met Gly Ser Arg Leu
145                 150                 155                 160

Val Gly Ile Ile Ser Ser Arg Asp Ile Asp Phe Leu Lys Glu Glu Glu
            165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
            195                 200                 205

Arg Ser Lys Lys Gly Lys Leu Pro Ile Val Asn Glu Asp Asp Glu Leu
210                 215                 220

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
            245                 250                 255

Gly Thr His Glu Asp Asp Lys Tyr Arg Leu Asp Leu Leu Ala Gln Ala
            260                 265                 270

Gly Val Asp Val Val Val Leu Asp Ser Ser Gln Gly Asn Ser Ile Phe
            275                 280                 285

Gln Ile Asn Met Ile Lys Tyr Ile Lys Asp Lys Tyr Pro Asn Leu Gln
            290                 295                 300

Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
            325                 330                 335

Cys Ile Thr Gln Glu Val Leu Ala Cys Gly Arg Pro Gln Ala Thr Ala
            340                 345                 350

Val Tyr Lys Val Ser Glu Tyr Ala Arg Arg Phe Gly Val Pro Val Ile
            355                 360                 365

Ala Asp Gly Gly Ile Gln Asn Val Gly His Ile Ala Lys Ala Leu Ala
            370                 375                 380
```

| | | | | | | | | | | | | |
|---|---|---|---|---|---|---|---|---|---|---|---|---|
| Leu | Gly | Ala | Ser | Thr | Val | Met | Met | Gly | Ser | Leu | Leu | Ala | Ala | Thr | Thr |
| 385 | | | | | 390 | | | | | 395 | | | | | 400 |

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
            405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
            435                 440                 445

Val Ser Gly Ala Val Gln Asp Lys Gly Ser Ile His Lys Phe Val Pro
            450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Gly Val His Ser Leu
            500                 505                 510

His Ser Tyr Glu Lys Arg Leu Phe
            515                 520

<210> SEQ ID NO 19
<211> LENGTH: 1563
<212> TYPE: DNA
<213> ORGANISM: Homo sapiens
<220> FEATURE:
<221> NAME/KEY: mutation
<222> LOCATION: (4)..(21)
<223> OTHER INFORMATION: insertion
<220> FEATURE:
<221> NAME/KEY: misc_feature
<222> LOCATION: (350)..(555)
<223> OTHER INFORMATION: subdomain

<400> SEQUENCE: 19

```
atgcatcacc atcaccatca cgccgactac ctgattagtg ggggcacgtc ctacgtgcca      60
gacgacggac tcacagcaca gcagctcttc aactgcggag acggcctcac ctacaatgac     120
tttctcattc tccctgggta catcgacttc actgcagacc aggtggacct gacttctgct     180
ctgaccaaga aaatcactct taagaccccca ctggtttcct ctcccatgga cacagtcaca     240
gaggctggga tggccatagc aatggcgctt acaggcggta ttggcttcat ccaccacaac     300
tgtacacctg aattccaggc caatgaagtt cggaaagtga agaaatatga acagggattc     360
atcacagacc ctgtggtcct cagccccaag gatcgcgtgc gggatgtttt tgaggccaag     420
gcccggcatg gtttctgcgg tatcccaatc acagacacag gccgatggg gagccgcttg     480
gtgggcatca tctcctccga agacattgat tttctcgagg aggaggaaca tgactgtttc     540
ttggaagaga taatgacaaa gagggaagac ttggtggtag cccctgcagg catcacactg     600
aaggaggcaa atgaaattct gcagcgcagc aagaagggaa agttgcccat tgtaaatgaa     660
gatgatgagc ttgtggccat cattgcccgg acagacctga gaagaatcg ggactaccca     720
ctagcctcca agatgccaa gaaacagctg ctgtgtgggg cagccattgg cactcatgag     780
gatgacaagt ataggctgga cttgctcgcc caggctggtg tggatgtagt ggttttggac     840
tcttcccagg gaaattccat cttccagatc aatatgatca agtacatcaa agacaaatac     900
cctaatctcc aagtcattgg aggcaatgtg gtcactgctg cccaggccaa gaacctcatt     960
gatgcaggtg tggatgccct gcgggtgggc atgggaagtg gctccatctg cattacgcag    1020
gaagtgctgg cctgtgggcg gccccaagca acagcagtgt acaaggtgtc agagtatgca    1080
```

-continued

```
cggcgctttg gtgttccggt cattgctgat ggaggaatcc aaaatgtggg tcatattgcg   1140
aaagccttgg cccttggggc ctccacagtc atgatgggct ctctcctggc tgccaccact   1200
gaggcccctg gtgaatactt cttttccgat gggatccggc taaagaaata tcgcggtatg   1260
ggttctctcg atgccatgga caagcacctc agcagccaga acagatattt cagtgaagct   1320
gacaaaatca aagtggccca gggagtgtct ggtgctgtgc aggacaaagg gtcaatccac   1380
aaatttgtcc cttacctgat tgctggcatc caacactcat gccaggacat tggtgccaag   1440
agcttgaccc aagtccgagc catgatgtac tctggggagc ttaagtttga gaagagaacg   1500
tcctcagccc aggtggaagg tggcgtccat agcctccatt cgtatgagaa gcggcttttc   1560
tga                                                                 1563
```

<210> SEQ ID NO 20
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag
<220> FEATURE:
<221> NAME/KEY: MISC_FEATURE
<222> LOCATION: (167)..(167)
<223> OTHER INFORMATION: mutation
<220> FEATURE:
<221> NAME/KEY: MISC_FEATURE
<222> LOCATION: (173)..(173)
<223> OTHER INFORMATION: mutation

<400> SEQUENCE: 20

```
Met His His His His His His Ala Asp Tyr Leu Ile Ser Gly Gly Thr
1               5                   10                  15

Ser Tyr Val Pro Asp Asp Gly Leu Thr Ala Gln Gln Leu Phe Asn Cys
            20                  25                  30

Gly Asp Gly Leu Thr Tyr Asn Asp Phe Leu Ile Leu Pro Gly Tyr Ile
        35                  40                  45

Asp Phe Thr Ala Asp Gln Val Asp Leu Thr Ser Ala Leu Thr Lys Lys
    50                  55                  60

Ile Thr Leu Lys Thr Pro Leu Val Ser Ser Pro Met Asp Thr Val Thr
65                  70                  75                  80

Glu Ala Gly Met Ala Ile Ala Met Ala Leu Thr Gly Gly Ile Gly Phe
                85                  90                  95

Ile His His Asn Cys Thr Pro Glu Phe Gln Ala Asn Glu Val Arg Lys
            100                 105                 110

Val Lys Lys Tyr Glu Gln Gly Phe Ile Thr Asp Pro Val Val Leu Ser
        115                 120                 125

Pro Lys Asp Arg Val Arg Asp Val Phe Glu Ala Lys Ala Arg His Gly
    130                 135                 140

Phe Cys Gly Ile Pro Ile Thr Asp Thr Gly Arg Met Gly Ser Arg Leu
145                 150                 155                 160

Val Gly Ile Ile Ser Ser Glu Asp Ile Asp Phe Leu Glu Glu Glu Glu
                165                 170                 175

His Asp Cys Phe Leu Glu Glu Ile Met Thr Lys Arg Glu Asp Leu Val
            180                 185                 190

Val Ala Pro Ala Gly Ile Thr Leu Lys Glu Ala Asn Glu Ile Leu Gln
        195                 200                 205

Arg Ser Lys Lys Gly Lys Leu Pro Ile Val Asn Glu Asp Asp Glu Leu
    210                 215                 220
```

Val Ala Ile Ile Ala Arg Thr Asp Leu Lys Lys Asn Arg Asp Tyr Pro
225                 230                 235                 240

Leu Ala Ser Lys Asp Ala Lys Lys Gln Leu Leu Cys Gly Ala Ala Ile
            245                 250                 255

Gly Thr His Glu Asp Asp Lys Tyr Arg Leu Asp Leu Leu Ala Gln Ala
        260                 265                 270

Gly Val Asp Val Val Leu Asp Ser Ser Gln Gly Asn Ser Ile Phe
    275                 280                 285

Gln Ile Asn Met Ile Lys Tyr Ile Lys Asp Lys Tyr Pro Asn Leu Gln
290                 295                 300

Val Ile Gly Gly Asn Val Val Thr Ala Ala Gln Ala Lys Asn Leu Ile
305                 310                 315                 320

Asp Ala Gly Val Asp Ala Leu Arg Val Gly Met Gly Ser Gly Ser Ile
            325                 330                 335

Cys Ile Thr Gln Glu Val Leu Ala Cys Gly Arg Pro Gln Ala Thr Ala
        340                 345                 350

Val Tyr Lys Val Ser Glu Tyr Ala Arg Arg Phe Gly Val Pro Val Ile
    355                 360                 365

Ala Asp Gly Gly Ile Gln Asn Val Gly His Ile Ala Lys Ala Leu Ala
370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
            405                 410                 415

Tyr Arg Gly Met Gly Ser Leu Asp Ala Met Asp Lys His Leu Ser Ser
        420                 425                 430

Gln Asn Arg Tyr Phe Ser Glu Ala Asp Lys Ile Lys Val Ala Gln Gly
    435                 440                 445

Val Ser Gly Ala Val Gln Asp Lys Gly Ser Ile His Lys Phe Val Pro
450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
            485                 490                 495

Glu Lys Arg Thr Ser Ser Ala Gln Val Glu Gly Gly Val His Ser Leu
        500                 505                 510

His Ser Tyr Glu Lys Arg Leu Phe
    515                 520

<210> SEQ ID NO 21
<211> LENGTH: 1563
<212> TYPE: DNA
<213> ORGANISM: Homo sapiens
<220> FEATURE:
<221> NAME/KEY: mutation
<222> LOCATION: (4)..(21)
<223> OTHER INFORMATION: insertion
<220> FEATURE:
<221> NAME/KEY: misc_feature
<222> LOCATION: (350)..(555)
<223> OTHER INFORMATION: subdomain

<400> SEQUENCE: 21
atgcatcacc atcaccatca cgccgactac ctgattagtg ggggcacgtc ctacgtgcca      60
gacgacggac tcagcacaca gcagctcttc aactgcggag acggcctcac ctacaatgac     120
tttctcattc tccctgggta catcgacttc actgcagacc aggtggacct gacttctgct     180

-continued

```
ctgaccaaga aaatcactct taagacccca ctggtttcct ctcccatgga cacagtcaca        240
gaggctggga tggccatagc aatggcgctt acaggcggta ttggcttcat ccaccacaac        300
tgtacacctg aattccaggc caatgaagtt cggaaagtga agaaatatga cagggattc         360 atcacagacc ctgtggtcct cagccccgaa gatgaggtgg aagatgtttt tgaggccgaa        420
gccgagcatg gttctgcgg tatcccaatc acagacacag gcgaaatggg aagcgagttg         480
gtgggcatca tctcctccag ggacattgat tttctcaaag aggaggaaca tgactgtttc        540
ttggaagaga taatgacaaa gagggaagac ttggtggtag cccctgcagg catcacactg        600
aaggaggcaa atgaaattct gcagcgcagc aagaagggaa agttgcccat tgtaaatgaa        660
gatgatgagc ttgtggccat cattgcccgg acagacctga agaagaatcg ggactaccca        720
ctagcctcca aagatgccaa gaaacagctg ctgtgtgggg cagccattgg cactcatgag        780
gatgacaagt ataggctgga cttgctcgcc caggctggtg tggatgtagt ggttttggac        840
tcttcccagg gaaattccat cttccagatc aatatgatca agtacatcaa agacaaatac        900
cctaatctcc aagtcattgg aggcaatgtg gtcactgctg cccaggccaa gaacctcatt        960
gatgcaggtg tggatgccct gcgggtgggc atgggaagtg gctccatctg cattacgcag        1020
gaagtgctgg cctgtgggcg gccccaagca acagcagtgt acaaggtgtc agagtatgca        1080
cggcgctttg gtgttccggt cattgctgat ggaggaatcc aaaatgtggg tcatattgcg        1140
aaagccttgg cccttgggc ctccacagtc atgatgggct ctctcctggc tgccaccact         1200
gaggcccctg gtgaatactt cttttccgat gggatccggc taaagaaata tcgcggtatg        1260
ggttctctcg atgccatgga caagcacctc agcagccaga acagatattt cagtgaagct        1320
gacaaaatca aagtggccca gggagtgtct ggtgctgtgc aggacaaagg gtcaatccac        1380
aaatttgtcc cttacctgat tgctggcatc caacactcat gccaggacat tggtgccaag        1440
agcttgaccc aagtccgagc catgatgtac tctggggagc ttaagtttga gaagagaacg        1500
tcctcagccc aggtggaagg tggcgtccat agcctccatt cgtatgagaa gcggcttttc        1560
tga                                                                      1563
```

<210> SEQ ID NO 22
<211> LENGTH: 520
<212> TYPE: PRT
<213> ORGANISM: Homo sapiens
<220> FEATURE:
<221> NAME/KEY: MISC_FEATURE
<222> LOCATION: (2)..(7)
<223> OTHER INFORMATION: his tag
<220> FEATURE:
<221> NAME/KEY: MISC_FEATURE
<222> LOCATION: (130)..(130)
<223> OTHER INFORMATION: mutation
<220> FEATURE:
<221> NAME/KEY: MISC_FEATURE
<222> LOCATION: (132)..(132)
<223> OTHER INFORMATION: mutation
<220> FEATURE:
<221> NAME/KEY: MISC_FEATURE
<222> LOCATION: (134)..(134)
<223> OTHER INFORMATION: mutation
<220> FEATURE:
<221> NAME/KEY: MISC_FEATURE
<222> LOCATION: (140)..(140)
<223> OTHER INFORMATION: mutation
<220> FEATURE:
<221> NAME/KEY: MISC_FEATURE
<222> LOCATION: (142)..(142)
<223> OTHER INFORMATION: mutation
<220> FEATURE:

```
<221> NAME/KEY: MISC_FEATURE
<222> LOCATION: (155)..(155)
<223> OTHER INFORMATION: mutation
<220> FEATURE:
<221> NAME/KEY: MISC_FEATURE
<222> LOCATION: (159)..(159)
<223> OTHER INFORMATION: mutation

<400> SEQUENCE: 22
```

| | | | | | | | | | | | | | | |
|---|---|---|---|---|---|---|---|---|---|---|---|---|---|---|
| Met | His | His | His | His | His | Ala | Asp | Tyr | Leu | Ile | Ser | Gly | Gly | Thr |
| 1 | | | | 5 | | | | | 10 | | | | | 15 |
| Ser | Tyr | Val | Pro | Asp | Asp | Gly | Leu | Thr | Ala | Gln | Gln | Leu | Phe | Asn | Cys |
| | | | 20 | | | | | 25 | | | | | 30 | | |
| Gly | Asp | Gly | Leu | Thr | Tyr | Asn | Asp | Phe | Leu | Ile | Leu | Pro | Gly | Tyr | Ile |
| | | | 35 | | | | | 40 | | | | | 45 | | |
| Asp | Phe | Thr | Ala | Asp | Gln | Val | Asp | Leu | Thr | Ser | Ala | Leu | Thr | Lys | Lys |
| | 50 | | | | | 55 | | | | | 60 | | | | |
| Ile | Thr | Leu | Lys | Thr | Pro | Leu | Val | Ser | Ser | Pro | Met | Asp | Thr | Val | Thr |
| 65 | | | | | 70 | | | | | 75 | | | | | 80 |
| Glu | Ala | Gly | Met | Ala | Ile | Ala | Met | Ala | Leu | Thr | Gly | Gly | Ile | Gly | Phe |
| | | | | 85 | | | | | 90 | | | | | 95 | |
| Ile | His | His | Asn | Cys | Thr | Pro | Glu | Phe | Gln | Ala | Asn | Glu | Val | Arg | Lys |
| | | | | 100 | | | | | 105 | | | | | 110 | |
| Val | Lys | Lys | Tyr | Glu | Gln | Gly | Phe | Ile | Thr | Asp | Pro | Val | Val | Leu | Ser |
| | | | 115 | | | | | 120 | | | | | 125 | | |
| Pro | Glu | Asp | Glu | Val | Glu | Asp | Val | Phe | Glu | Ala | Glu | Ala | Glu | His | Gly |
| | 130 | | | | | 135 | | | | | 140 | | | | |
| Phe | Cys | Gly | Ile | Pro | Ile | Thr | Asp | Thr | Gly | Glu | Met | Gly | Ser | Glu | Leu |
| 145 | | | | | 150 | | | | | 155 | | | | | 160 |
| Val | Gly | Ile | Ile | Ser | Ser | Arg | Asp | Ile | Asp | Phe | Leu | Lys | Glu | Glu | Glu |
| | | | | 165 | | | | | 170 | | | | | 175 | |
| His | Asp | Cys | Phe | Leu | Glu | Glu | Ile | Met | Thr | Lys | Arg | Glu | Asp | Leu | Val |
| | | | 180 | | | | | 185 | | | | | 190 | | |
| Val | Ala | Pro | Ala | Gly | Ile | Thr | Leu | Lys | Glu | Ala | Asn | Glu | Ile | Leu | Gln |
| | | | 195 | | | | | 200 | | | | | 205 | | |
| Arg | Ser | Lys | Lys | Gly | Lys | Leu | Pro | Ile | Val | Asn | Glu | Asp | Asp | Glu | Leu |
| | 210 | | | | | 215 | | | | | 220 | | | | |
| Val | Ala | Ile | Ile | Ala | Arg | Thr | Asp | Leu | Lys | Lys | Asn | Arg | Asp | Tyr | Pro |
| 225 | | | | | 230 | | | | | 235 | | | | | 240 |
| Leu | Ala | Ser | Lys | Asp | Ala | Lys | Lys | Gln | Leu | Leu | Cys | Gly | Ala | Ala | Ile |
| | | | 245 | | | | | 250 | | | | | 255 | | |
| Gly | Thr | His | Glu | Asp | Asp | Lys | Tyr | Arg | Leu | Asp | Leu | Leu | Ala | Gln | Ala |
| | | | 260 | | | | | 265 | | | | | 270 | | |
| Gly | Val | Asp | Val | Val | Val | Leu | Asp | Ser | Ser | Gln | Gly | Asn | Ser | Ile | Phe |
| | | | 275 | | | | | 280 | | | | | 285 | | |
| Gln | Ile | Asn | Met | Ile | Lys | Tyr | Ile | Lys | Asp | Lys | Tyr | Pro | Asn | Leu | Gln |
| | 290 | | | | | 295 | | | | | 300 | | | | |
| Val | Ile | Gly | Gly | Asn | Val | Val | Thr | Ala | Ala | Gln | Ala | Lys | Asn | Leu | Ile |
| 305 | | | | | 310 | | | | | 315 | | | | | 320 |
| Asp | Ala | Gly | Val | Asp | Ala | Leu | Arg | Val | Gly | Met | Gly | Ser | Gly | Ser | Ile |
| | | | | 325 | | | | | 330 | | | | | 335 | |
| Cys | Ile | Thr | Gln | Glu | Val | Leu | Ala | Cys | Gly | Arg | Pro | Gln | Ala | Thr | Ala |
| | | | 340 | | | | | 345 | | | | | 350 | | |
| Val | Tyr | Lys | Val | Ser | Glu | Tyr | Ala | Arg | Arg | Phe | Gly | Val | Pro | Val | Ile |
| | | | 355 | | | | | 360 | | | | | 365 | | |

-continued

```
Ala Asp Gly Gly Ile Gln Asn Val Gly His Ile Ala Lys Ala Leu Ala
    370                 375                 380

Leu Gly Ala Ser Thr Val Met Met Gly Ser Leu Leu Ala Ala Thr Thr
385                 390                 395                 400

Glu Ala Pro Gly Glu Tyr Phe Phe Ser Asp Gly Ile Arg Leu Lys Lys
                405                 410                 415

Tyr Arg Gly Met Gly Ser Leu Asp Ala Met Asp Lys His Leu Ser Ser
            420                 425                 430

Gln Asn Arg Tyr Phe Ser Glu Ala Asp Lys Ile Lys Val Ala Gln Gly
        435                 440                 445

Val Ser Gly Ala Val Gln Asp Lys Gly Ser Ile His Lys Phe Val Pro
    450                 455                 460

Tyr Leu Ile Ala Gly Ile Gln His Ser Cys Gln Asp Ile Gly Ala Lys
465                 470                 475                 480

Ser Leu Thr Gln Val Arg Ala Met Met Tyr Ser Gly Glu Leu Lys Phe
                485                 490                 495

Glu Lys Arg Thr Ser Ser Ala Gln Val Glu Gly Gly Val His Ser Leu
            500                 505                 510

His Ser Tyr Glu Lys Arg Leu Phe
        515                 520
```

METHODS FOR PRODUCING RECOMBINANT HISTIDINE-TAGGED INOSINE NONOPHOSPHATE DEHYDROGENASE POLYPEPTIDES

RELATED APPLICATIONS

This application is a divisional of U.S. Pat. No. 10/769,481 filed Jan. 30. 2004 which is now U.S Pat. No. 7276,362 issued Oct. 2. 2007.

FIELD OF THE INVENTION

The present invention relates to modified inosine monophosphate dehydrogenases. More particularly, the invention relates to histidine-tagged modified inosine monophosphate dehydrogenases wherein the modified enzymes have stabilized activity relative to wild-type inosine monophosphate dehydrogenases.

BACKGROUND OF THE INVENTION

Inosine-5'-monophosphate dehydrogenase (IMPDH; EC 1.1.1.205) is a key enzyme in the de novo synthesis of purines. IMPDH catalyzes the NAD-dependent oxidation of inosine-5'-monophosphate (IMP) to xanthosine-5'-monophosphate (XMP), resulting in the production of NADH and XMP. IMPDH catalyzed oxidation of IMP to XMP is the rate-limiting step in the synthesis of guanine nucleotides.

IMPDH exists as a homotetramer (i.e., the enzyme has four subunits each comprising an IMPDH polypeptide). In many species, two isoforms of IMPDH have been described and are designated type I and type II IMPDH. Human type I and type II IMPDH have been identified and sequenced. Human IMPDH types I and II are both 514 amino acids in length and they share 84% sequence identity. The nucleotide and amino acid sequence of human type I IMPDH are disclosed in Natsumeda, Y., et al., *J. Biol. Chem.* 265:5292-5295 (1990), and the nucleotide and amino acid sequence of human type II IMPDH are disclosed in Natsumeda, Y., et al., *J. Biol. Chem.* 265:5292-5295 (1990), Collart, F. R. and Hubermann, E., *J. Biol. Chem.* 263:15769-15772 (1988), and U.S. Pat. No. 5,665,583. The subunits of human IMPDH types I and II that make up the IMPDH homotetramer each have a subunit molecular weight of 56 kDa. Human type II IMPDH has a catalytic core domain (amino acids 1-109 and 245-514) and a subdomain (amino acids 110-244) with unknown function.

IMPDH is a target for antitumor (e.g., antileukemic) therapy and immunosuppressive chemotherapy. IMPDH is upregulated in neoplastic and differentiating cells. Furthermore, proliferating B and T lymphocytes depend on the de novo pathway, rather than the salvage pathway, for synthesis of guanine nucleotides with inhibition of guanine nucleotide synthesis resulting in inhibition of DNA synthesis. Thus, IMPDH is an important enzyme for B and T cell proliferation, and inhibition of IMPDH activity inhibits both B and T cell proliferation making IMPDH an important target for immunosuppressive chemotherapy.

Mycophenolic acid (MPA) is an uncompetitive inhibitor of human types I and II IMPDH and MPA binds IMPDH after NADH is released, but before XMP is produced. MPA is the active metabolite in vivo of the ester prodrug mycophenolate mofetil (CellCept; MMF). MMF is an immunosuppressant that blocks B and T cell proliferation and MMF has been approved for the treatment of kidney and heart transplant rejection. MMF has also been used clinically to treat cancer and viral infections, and has been used as an anti-vascular hyperproliferative agent, an antipsoriatric agent, an antibacterial agent, an antifungal agent, and has been used for the treatment of autoimmune diseases.

MMF is hydrolyzed to MPA in vivo, and, accordingly, the monitoring of MPA levels in vivo allows for monitoring of MMF dosages. The measurement of MPA levels in patients treated with MMF is of clinical significance because the monitoring of MPA levels improves therapeutic efficacy, e.g., optimal MMF levels necessary for adequate immunosuppression can be determined, and minimizes the adverse side effects of the drug. Isolated, recombinant IMPDH has been used in assays to measure MPA levels in patients treated with MMF, such as the assays described in U.S. Pat. Nos. 6,107, 052 and 6,524,808.

The ability to produce and to isolate large amounts of stable, recombinant IMPDH (e.g., IMPDH that aggregates minimally) is important for use in assays for monitoring MPA levels in patients treated with MMF, or for use in assays to monitor the levels in patient samples of any other therapeutically useful IMPDH inhibitor. Other inhibitors of IMPDH are described in Anderson, J. H. et al., *J. Biol. Chem.* 243: 4762-4768 (1968) and in U.S. Pat. Nos. 5,380,879, 5,444, 072, and 5,807,876 and in PCT publications WO 94/01105 and WO 94/12184.

The ability to produce and to isolate large amounts of stable, recombinant IMPDH is also important for other clinical and research applications, such as for the identification and design of new IMPDH inhibitors useful for cancer and immunosuppressive therapies, and for determining the sensitivity of IMPDH to those inhibitors.

SUMMARY OF THE INVENTION

The present invention is directed to modified recombinant IMPDH polypeptides, and to isolated, modified nucleic acid molecules encoding these modified recombinant IMPDH polypeptides. The invention is also directed to a method, vectors, and host cells for producing such a modified recombinant IMPDH polypeptide, and to kits comprising the modified IMPDH polypeptide. The recombinant IMPDH polypeptides are modified to contain a histidine tag for purification by nickel chelate affinity chromatography, and are also modified in the subdomain region of the polypeptides so that the rate stability of the histidine-tagged, modified IMPDH polypeptides is maintained relative to the wild-type IMPDH polypeptide.

In one embodiment, the histidine-tagged, modified IMPDH polypeptide has the amino acid sequence as shown in any one of SEQ ID NOS: 14, 16, 18, 20, or 22. In another embodiment, one or more of the amino acids at positions 116-250 as shown in SEQ ID NO: 12 are substituted in the histidine-tagged, modified IMPDH polypeptide with a negatively charged amino acid. In still another embodiment, one or more of the positively charged amino acids at positions 130, 132, 134, 140, 142, 143, 155, 159, 167, 173, 177, 187, 188, 201, 209, 211, 212, 214, 230, 234, 235, 237, 244, 247, or 248 as shown in SEQ ID NO: 12 are substituted in the histidine-tagged, modified IMPDH polypeptide with a negatively charged amino acid. In an alternative embodiment, one or more of the positively charged amino acids at positions 130, 132, 134, 140, 142, 155, 159, 167, or 173 as shown in SEQ ID NO: 12 are substituted in the histidine-tagged, modified IMPDH polypeptide with a negatively charged amino acid.

Also provided are isolated nucleic acid molecules encoding the histidine-tagged, modified IMPDH polypeptides. Accordingly, the isolated nucleic acid molecules provided herein encode a modified type I or type II IMPDH polypeptide wherein the modified IMPDH polypeptide has a histidine tag and wherein the subdomain of the IMPDH polypeptide is modified so that the rate stability of the histidine-tagged, modified IMPDH polypeptide is maintained relative to the wild-type IMPDH polypeptide. In one embodiment, the isolated nucleic acid molecule can comprise a sequence selected from the group consisting of SEQ ID NO: 13, SEQ ID NO: 15, SEQ ID NO: 17, SEQ ID NO: 19, SEQ ID NO: 21, and complementary sequences thereof. In another embodiment, isolated nucleic acid molecules are provided wherein the complementary sequences of the isolated nucleic acid molecules hybridize under stringent conditions to any one of the nucleotide sequences set forth in SEQ ID NO: 13, 15, 17, 19, or 21.

In still another embodiment, isolated nucleic acid molecules are provided wherein the complementary sequences of the isolated nucleic acid molecules hybridize under stringent conditions to nucleotides 346-750 of a sequence selected from the group consisting of SEQ ID NO: 13, SEQ ID NO: 15, SEQ ID NO: 17, SEQ ID NO: 19, and SEQ ID NO: 21. In still another embodiment, isolated nucleic acid molecules are provided comprising nucleotides 346-750 of a sequence selected from the group consisting of SEQ ID NO: 13, SEQ ID NO: 15, SEQ ID NO: 17, SEQ ID NO: 19, and SEQ ID NO: 21. In another embodiment, isolated nucleic acid molecules are provided wherein the IMPDH polypeptide encoded comprises an amino sequence selected from the group consisting of SEQ ID NO: 14, SEQ ID NO: 16, SEQ ID NO: 18, SEQ ID NO: 20, and SEQ ID NO: 22. In still another embodiment, a vector is provided comprising the isolated nucleic acid molecule of SEQ ID NO: 13, SEQ ID NO: 15, SEQ ID NO: 17, SEQ ID NO: 19, or SEQ ID NO: 21 obtainable from *E. coli* H712 and having ATCC accession number PTA-5786, PTA-5782, PTA-5784, PTA-5785, and PTA-5783, respectively.

BRIEF DESCRIPTION OF THE DRAWINGS

FIG. 3 shows the nucleotide sequences of the PCR primers ((+) and (−)) used to incorporate the coding sequence for a histidine tag into the 5'-end of the human wild-type, IMPDH type II coding sequence (SEQ ID NO: 1 and SEQ ID NO: 2). FIG. 3 also shows the nucleotide sequences of the PCR primers ((+) and (−)) used to mutate, by site-directed mutagenesis, the histidine-tagged human wild-type, IMPDH type II sequence in regions of the coding sequence corresponding to amino acids 130-142 (SEQ ID NO: 3 and SEQ ID NO: 4), 155-159 (SEQ ID NO: 5 and SEQ ID NO: 6), and 167-173 (SEQ ID NO: 7 and SEQ ID NO: 8).

FIG. 4 shows the nucleotide sequence of human wild-type, IMPDH type II (SEQ ID NO: 9).

FIG. 5 A and B show the deduced amino acid sequence of human wild-type, IMPDH type II (SEQ ID NO: 10). The subdomain is underlined.

FIG. 6 shows the nucleotide sequence of human wild-type, IMPDH type II with coding sequence for a histidine tag incorporated into the 5'-end of the coding sequence (SEQ ID NO: 11).

FIGS. 7 A and B show the deduced amino acid sequence of human wild-type, IMPDH type II with a histidine tag incorporated into the amino-terminal end of the polypeptide (SEQ ID NO: 12). The subdomain is underlined and the amino acids encoding the histidine tag are in italics.

FIG. 8 shows the nucleotide sequence of human IMPDH type II Δ 2B+AH clone A (SEQ ID NO: 13).

FIGS. 9 A and B show the deduced amino acid sequence of human IMPDH type II Δ 2B+AH clone A (SEQ ID NO: 14). The subdomain is underlined and the amino acids encoding the histidine tag, and the amino acid substitutions in the subdomain, are in italics.

FIG. 10 shows the nucleotide sequence of human IMPDH type II (Δ 3+1A)+AH clone A (SEQ ID NO: 15).

FIGS. 11 A and B show the deduced amino acid sequence of human IMPDH type II (Δ 3+1A)+AH clone A (SEQ ID NO: 16). The subdomain is underlined and the amino acids encoding the histidine tag, and the amino acid substitutions in the subdomain, are in italics.

FIG. 12 shows the nucleotide sequence of human IMPDH type II Δ 1,2A+AH clone B (SEQ ID NO: 17).

FIGS. 13 A and B show the deduced amino acid sequence of human Δ 1,2A+AH clone B IMPDH type II (SEQ ID NO: 18). The subdomain is underlined and the amino acids encoding the histidine tag, and the amino acid substitutions in the subdomain, are in italics.

FIG. 14 shows the nucleotide sequence of human IMPDH type II Δ 3B+AH clone B (SEQ ID NO: 19).

FIGS. 15 A and B show the deduced amino acid sequence of human IMPDH type II Δ 3B+AH clone B (SEQ ID NO: 20). The subdomain is underlined and the amino acids encoding the histidine tag, and the amino acid substitutions in the subdomain, are in italics.

FIG. 16 shows the nucleotide sequence of human IMPDH type II (Δ 2 +1A) +AH clone B (SEQ ID NO: 21).

FIGS. 17 A and B show the deduced amino acid sequence of human IMPDH type II (Δ 2+1A)+AH clone B (SEQ ID NO: 22). The subdomain is underlined and the amino acids encoding the histidine tag, and the amino acid substitutions in the subdomain, are in italics.

DETAILED DESCRIPTION OF THE INVENTION

Figure 1:
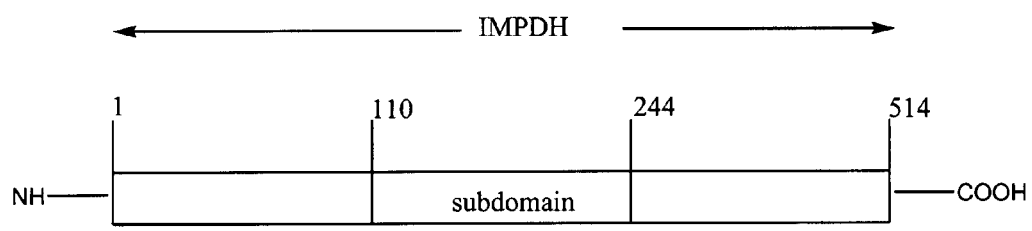
FIG. 1 is a schematic representation of a wild-type IMPDH polypeptide showing the catalytic core and subdomain regions of the wild-type IMPDH polypeptide. For the positions of amino acid substitutions made in the histidine-tagged, modified IMPDH polypeptides described herein, see FIGS. 9 A and B, 11 A and B, 13 A and B, 15 A and B, and 17 A and B.

The present invention is directed to histidine-tagged, modified recombinant IMPDH polypeptides, and to isolated, modified nucleic acid molecules encoding these IMPDH polypeptides. The invention is also directed to a method, vectors, and host cells for producing such a histidine-tagged, modified recombinant IMPDH polypeptide, and to kits comprising the modified IMPDH polypeptide. The recombinant IMPDH polypeptides are modified to contain a histidine tag for purification by nickel chelate affinity chromatography, and are also modified in the subdomain region of the polypeptides (see FIG. 1) so that the rate stability of the histidine-tagged, modified IMPDH polypeptides is maintained relative to the wild-type IMPDH polypeptide.

Purification of the wild-type IMPDH enzyme results in low yields and low purity. Accordingly, an affinity tag, such as a 6-histidine tag, is often incorporated into wild-type IMPDH to shorten purification time and increase yield and purity. The addition of such affinity tags can result in decreased solubility and stability of IMPDH in solution. Accordingly, nucleic acid molecules encoding histidine-tagged human IMPDH polypeptides were modified by site-directed mutagenesis as described herein to encode amino acid substitutions in the subdomain region of the polypeptides. These amino acid substitutions result in maintenance of the rate stability of the histidine-tagged, modified IMPDH polypeptides relative to the wild-type IMPDH polypeptide (see FIGS. 18-24).

Maintenance of the rate stability of the histidine-tagged, modified IMPDH polypeptide relative to the wild-type IMPDH polypeptide means that the rate stability of the histidine-tagged, modified IMPDH polypeptide at 4° C. is at least about 80% of the rate stability of the wild-type IMPDH polypeptide, at least about 85% of the rate stability of the wild-type IMPDH polypeptide, at least about 95% of the rate stability of the wild-type IMPDH polypeptide, or at least about 98% of the rate stability of the wild-type IMPDH polypeptide.

As used herein, the term "modified IMPDH polypeptide" refers to an IMPDH polypeptide having the IMPDH subdomain (i.e., internal non-catalytic subdomain) of the wild-type IMPDH polypeptide modified by substitution of at least one amino acid normally present in the subdomain with an amino acid not normally present. The "modified IMPDH polypeptides" are functionally catalytic and may form a multimer (e.g., a homotetramer) which is also a "modified IMPDH polypeptide" in accordance with the present invention. The "modified IMPDH polypeptides" described herein are typically recombinant, but can be synthetic.

As used herein, the term "complementary sequence" refers to the ability of purine and pyrimidine nucleotide sequences to associate through hydrogen bonding to form double-stranded nucleic acid molecules. Guanine and cytosine, adenine and thymine, and adenine and uracil are complementary and can associate through hydrogen bonding resulting in the formation of double-stranded nucleic acid molecules when two nucleic acid molecules have "complementary" sequences. The complementary sequences can be DNA or RNA sequences.

As used herein, an "isolated" nucleic acid molecule is a nucleic acid molecule that is substantially separated from other contaminant nucleic acid molecules that encode a different polypeptide.

The single letter codes for amino acids are as follows: A=alanine, R=arginine, N=asparagine, D=aspartic acid, C=cysteine, Q=glutamine, E=glutamic acid, G=glycine, H=histidine, I=isoleucine, L=leucine, K=lysine, M=methionine, F=phenylalanine, P=proline, S=serine, T=threonine, W=tryptophan, Y=tyrosine, and V=valine.

Type I and type II IMPDH polypeptides include an N-terminal catalytic domain, an internal non-catalytic subdomain, and a C-terminal catalytic domain (see FIG. 1). Type I or type II IMPDH polypeptides from a variety of species can be histidine-tagged, and modified in the subdomain region of the polypeptides as described herein to produce and isolate, in high yield and purity, stabilized histidine-tagged recombinant IMPDH polypeptides. The histidine-tag can be of any length useful for purification of proteins by nickel chelate affinity chromatography.

The type I or type II IMPDH polypeptides provided herein that have been modified to contain a histidine tag, and have been modified in the IMPDH subdomain can be further substituted, deleted, truncated, or fused with other polypeptides, or combinations thereof, as long as the resulting expressed IMPDH polypeptide, or a fragment thereof, retains substantially the same IMPDH activity as the histidine-tagged, modified IMPDH polypeptides exemplified herein. These substituted, deleted, truncated, and fused polypeptides are considered equivalents of the exemplified modified IMPDH polypeptides and are within the scope of the present invention.

"Further substituted" means that the equivalent differs by one or more amino acid substitution from the IMPDH polypeptides described herein and the further substitution can be conservative or nonconservative and the further substitution can be with an amino acid analog. The further substitution can also be made to optimize the level of production of the modified IMPDH polypeptide in a particular prokaryotic or eukaryotic host cell (i.e., a codon-usage variant). The further substitution can occur either in the subdomain or in any other portion of the IMPDH polypeptide (e.g., in the N-terminal catalytic domain or in the C-terminal catalytic domain).

In one embodiment, a modified type I or II IMPDH polypeptide is provided. The modified IMPDH polypeptide has a histidine tag and the subdomain of the IMPDH polypeptide is modified so that the rate stability of the histidine-tagged, modified IMPDH polypeptide is maintained relative to the wild-type IMPDH polypeptide. In other embodiments, the modified IMPDH polypeptide has the amino acid sequence as shown in any one of SEQ ID NOS: 14, 16, 18, 20, or 22. In the embodiment shown in SEQ ID NO: 14, each of the arginines at positions 155 and 159 (see SEQ ID NO: 12) are substituted with a glutamic acid (SEQ ID NO: 14 positions 155 and 159). In the embodiment shown in SEQ ID NO: 16, the arginine at position 167, the lysine at position 173, and the valine at position 390 (see SEQ ID NO: 12) are substituted with a glutamic acid, a glutamic acid, and an aspartic acid, respectively (SEQ ID NO: 16 positions 167, 173, and 390). In the embodiment shown in SEQ ID NO: 18, the lysine at position 140 and the arginine at position 142 (see SEQ ID NO: 12) are substituted with a glutamic acid (SEQ ID NO: 18 positions 140 and 142). In the embodiment shown in SEQ ID NO: 20, the arginine at position 167 and the lysine at position 173 (see SEQ ID NO: 12) are substituted with a glutamic acid (SEQ ID NO: 20 positions 167 and 173). In the embodiment shown in SEQ ID NO: 22, the lysine at position 130, the arginine at position 132, the arginine at position 134, the lysine at position 140, the arginine at position 142, the arginine at position 155, and the arginine at position 159 (see SEQ ID NO: 12) are each substituted with a glutamic acid (SEQ ID NO: 22 positions 130, 132, 134, 140, 142, 155, and 159).

In yet another embodiment, one or more of the amino acids at positions 116-250 as shown in SEQ ID NO: 12 are substituted in the modified IMPDH polypeptide with a negatively charged amino acid, such as aspartic acid or glutamic acid. In still another embodiment, one or more of the positively charged amino acids at positions 130, 132, 134, 140, 142, 143, 155, 159, 167, 173, 177, 187, 188, 201, 209, 211, 212, 214, 230, 234, 235, 237, 244, 247, or 248 as shown in SEQ ID NO: 12 of are substituted in the modified IMPDH polypeptide with a negatively charged amino acid. In an alternative embodiment, one or more of the positively charged amino acids at positions 130, 132, 134, 140, 142, 155, 159, 167, or 173 as shown in SEQ ID NO: 12 are substituted in the modified IMPDH polypeptide with a negatively charged amino acid.

Exemplary of nucleic acid molecules encoding type I or type II IMPDH that can be modified in the IMPDH subdomain-encoding region of the nucleic acid molecules, and used to produce the histidine-tagged, modified IMPDH polypeptides described herein, include IMPDH-encoding nucleic acids from a human source or other mammalian sources, or bacterial, fungal, yeast, or plant sources. Any other type I or type II IMPDH-encoding nucleic acid molecule from a eukaryotic or prokaryotic source can also be used to produce histidine-tagged type I or type II IMPDH polypeptides modified in the subdomain region so that the rate stability of the histidine-tagged, modified IMPDH polypeptides relative to the wild-type IMPDH polypeptide is maintained.

In one embodiment, nucleic acid molecules obtained, for example, from isolated microorganisms, such as bacteria, fungus, or yeast, that exhibit particularly high IMPDH activity can be used. In another embodiment, the expressed IMPDH nucleic acid molecule can be a heterologous nucleic acid molecule and, in yet another embodiment, the expressed IMPDH nucleic acid molecule can be a homologous nucleic acid molecule. A heterologous nucleic acid molecule is defined herein as a nucleic acid molecule originating from a different species than the species used for expression of the nucleic acid molecule. A homologous nucleic acid molecule is defined herein as a nucleic acid molecule originating from the same species used for expression of the nucleic molecule.

Exemplary nucleic acid or amino acid sequences of IMPDH that can be used are described in Natsumeda et al., *J. Biol. Chem.* 265:5292-5295 (1990), Collart, F. R. and Hubermann, E., *J. Biol. Chem.* 263:15769-15772 (1988), U.S. Pat. No. 5,665,583, Gu et al., *J. Biol. Chem.* 272:4458-4466 (1997), Dayton et al., *J. Immunol.* 152:984 (1994), Zimmermann et al., *J. Biol. Chem.* 270:6808-6814 (1995), and Glesne et al., *Biochem. And Biophys. Res. Comm.* 537-544 (1994).

Type I or type II IMPDH-encoding nucleic acid molecules that have been modified to contain coding sequence for a histidine tag, and have been modified in the IMPDH subdomain-encoding region of the nucleic acid molecule that are further substituted, deleted, truncated, and/or fused with other nucleic acid molecules wherein the resulting expressed IMPDH polypeptide, or a fragment thereof, retains substantially the same IMPDH activity as the histidine-tagged, modified IMPDH polypeptides exemplified herein, are considered equivalents of the exemplified histidine-tagged, modified IMPDH polypeptides and are within the scope of the present invention.

Also within the scope of the invention are nucleic acid molecules complementary to the nucleic acid molecules that encode the histidine-tagged, modified IMPDH polypeptides described herein, and those that hybridize to the complementary nucleic acid molecules under stringent conditions. Typical stringent conditions include, for example, hybridization at 50° C. to 65° C. in 5×SSPE and 50% formamide, and washing at 50° C. to 65° C. in 0.5×SSPE, or hybridization at 65° C. in 0.1% SDS and 1×SSC. Other stringent conditions are described in Sambrook et al., "Molecular Cloning: A Laboratory Manual", 3rd Edition, Cold Spring Harbor Laboratory Press (2001), incorporated herein by reference.

The nucleic acid molecules that encode the histidine-tagged, modified IMPDH polypeptides described herein can be DNA or RNA and can be recombinant or synthetic. In one embodiment, the nucleic acid molecules are labeled with a detectable marker such as a radioisotope, a fluorescent compound, a bioluminescent compound, a chemiluminescent compound, a metal chelator or an enzyme, and are used as probes. In another embodiment, the nucleic acid molecules described herein include peptide nucleic acids (PNAs), or derivatives such as phosphorothioate, phosphotriester, phosphoramidate, and methylphosphonate, that specifically bind to single-stranded DNA or RNA (Goodchild, et al., *Proc. Natl. Acad. Sci.* 83:4143-4146 (1986)).

In yet another embodiment, the nucleic acid molecules that encode the histidine-tagged, modified IMPDH polypeptides are isolated. Techniques known in the art can be used to isolate the nucleic acid molecules encoding the histidine-tagged, modified IMPDH polypeptides described herein. Such a technique is described in more detail below, and other techniques for isolating nucleic acid molecules are described in Sambrook et al., "Molecular Cloning: A Laboratory Manual", 3rd Edition, Cold Spring Harbor Laboratory Press, (2001).

For example, the nucleic acid molecules that encode the histidine-tagged, modified IMPDH polypeptides can be generated by isolating a cDNA clone encoding the wild-type IMPDH protein. Recombinant DNA technology can then be used to alter the cDNA sequence to encode amino acid substitutions in the IMPDH subdomain, and to incorporate coding sequence for a histidine tag, for example, into the 5'-end of the IMPDH coding sequence. Alteration of the cDNA sequence can be accomplished, for example, by using PCR for site-directed mutagenesis to alter the cDNA sequence to encode amino acid substitutions in the IMPDH subdomain, or by using PCR to insert coding sequence for a histidine tag into the 5'-end of the IMPDH coding sequence (see U.S. Pat. No. 4,603,102, incorporated herein by reference).

Similar techniques were used to isolate the nucleic acid molecules encoding the histidine-tagged, modified IMPDH polypeptides described herein. PCR primers having the sequences of SEQ ID NOS: 1 and 2 (see FIG. 3) were used to insert coding sequence for a histidine tag into the 5'-end of the wild-type human type II IMPDH coding sequence in the plasmid pKK117 (see FIG. 2). PCR primers having the sequences of SEQ ID NOS: 3-8 (see FIG. 3) were used to alter the human type II IMPDH sequence in pKK117, having coding sequence for a histidine tag at the 5'-end, to produce nucleic acid molecules encoding the histidine-tagged, modified IMPDH polypeptides described herein (i.e., with amino acid substitutions in the IMPDH subdomain).

The resulting nucleic acid molecules and histidine-tagged, modified IMPDH polypeptides are denominated Δ 2B+AH clone A, (Δ 3+1A)+AH clone A, Δ 1,2A+AH clone B, Δ 3B+AH clone B, and (Δ 2+1A)+AH clone B. These clones have the nucleotide sequences shown in SEQ ID NOS: 13, 15, 17, 19, and 21, respectively (FIGS. 8, 10, 12, 14, and 16), and the deduced amino acid sequences shown in SEQ ID NOS: 14, 16, 18, 20, and 22, respectively (see FIGS. 9 A and B, 11 A and B, 13 A and B, 15 A and B, and 17 A and B). The human wild-type IMPDH type II coding sequence has the sequence of SEQ ID NO: 9 (FIG. 4), and the deduced amino acid sequence of SEQ ID NO: 10 (FIGS. 5 A and B). The coding sequence of human wild-type, IMPDH type II, with coding sequence for a histidine tag incorporated at the 5'-end of the molecule, has the nucleotide sequence of SEQ ID NO: 11 (FIG. 6), and the deduced amino acid sequence of SEQ ID NO: 12 (FIGS. 7 A and B).

All histidine-tagged wild-type and histidine-tagged, modified IMPDH-encoding nucleic acid molecules have been deposited in the American Type Culture Collection, 10801 University Blvd., Manassas, Va. Each of these nucleic acid molecules was inserted in pKK117 and the vector with insert was transformed into *E. coli* H712. The clones containing human wild-type, IMPDH type II DNA, with coding sequence for a histidine tag incorporated at the 5'-end of the molecule, and clones denominated Δ 2B+AH clone A, (Δ 3+1A)+AH clone A, Δ 1,2A+AH clone B, Δ 3B+AH clone B, and (Δ2+1A)+AH clone B, have ATCC accession numbers PTA-5787, PTA-5786, PTA-5782, PTA-5784, PTA-5785, and PTA-5783, respectively.

Thus, an isolated nucleic acid molecule is provided. The isolated nucleic acid molecule encodes a modified type I or type II IMPDH polypeptide where the IMPDH polypeptide has a histidine tag and where the subdomain of the IMPDH polypeptide is modified so that the rate stability of the histidine-tagged, modified IMPDH polypeptide is maintained relative to the wild-type IMPDH polypeptide. In one embodiment, the isolated nucleic acid molecule can comprise a sequence selected from the group consisting of SEQ ID NO: 13, SEQ ID NO: 15, SEQ ID NO: 17, SEQ ID NO: 19, SEQ ID) NO: 21, and complementary sequences thereof. In another embodiment, isolated nucleic acid molecules are provided wherein the complementary sequences of the isolated nucleic acid molecules hybridize under stringent conditions to any one of the nucleotide sequences set forth in SEQ ID NO: 13, 15, 17, 19, or 21.

In still another embodiment, isolated nucleic acid molecules are provided wherein the complementary sequences of the isolated nucleic acid molecules hybridize under stringent conditions to nucleotides 346-750 of a sequence selected from the group consisting of SEQ IID NO: 13, SEQ ID NO: 15, SEQ ID NO: 17, SEQ ID NO: 19, and SEQ ID NO: 21. In still another embodiment, isolated nucleic acid molecules are provided comprising nucleotides 346-750 of a sequence selected from the group consisting of SEQ ID NO: 13, SEQ ID NO: 15, SEQ ID NO: 17, SEQ ID NO: 19, and SEQ ID NO: 21. In another embodiment, isolated nucleic acid molecules are provided wherein the IMPDH polypeptide encoded comprises an amino sequence selected from the group consisting of SEQ ID NO: 14, SEQ ID NO: 16, SEQ ID NO: 18, SEQ ID NO: 20, and SEQ ID NO: 22. In still another embodiment, a vector is provided comprising the isolated nucleic acid molecule of SEQ ID NO: 13, SEQ ID NO: 15, SEQ ID NO: 17, SEQ ID) NO: 19, or SEQ ID NO: 21 obtainable from *E. coli* H712 and having ATCC accession numbers PTA-5786, PTA-5782, PTA-5784, PTA-5785, and PTA-5783, respectively.

Any prokaryotic or eukaryotic host cell-vector system known to the skilled artisan can be used for the expression of the histidine-tagged, modified IMPDH polypeptides described herein. For example, a system where the vector replicates autonomously or integrates into the host genome can be used. The term vector includes, but is not limited to, plasmids, cosmids, phage, phagmids, and modified viral vectors. Illustrative examples of prokaryotic expression vectors are BLUESCRIPT (Stratagene), pIN vectors (Van Heeke, et al., *J. Biol. Chem.* 264:5503-5509 (1989), incorporated herein by reference), pET24a for expression in *E. coli* (Novagen, Inc., Madison, Wis.), and pKK117 described herein. An illustrative example of a eukaryotic expression vector is an adenovirus expression vector for expression in eukaryotic cells (Logan, et al., *Proc. Natl. Acad. Sci.* 81:3655-59 (1984), incorporated herein by reference).

In one embodiment, the vector has restriction endonuclease cleavage sites for the insertion of nucleic acid molecules, and genetic markers for selection of host cell transformants (e.g., ampicillin, tetracycline, kanamycin, or neomycin resistance markers). In an expression vector, the IMPDH-encoding nucleic acid molecule can be operably linked to a promoter capable of directing the expression of the IMPDH polypeptide in a particular host cell-vector system. Exemplary prokaryotic promoters include constitutive promoters (e.g., the 3-phosphoglycerate kinase promoter or the α-factor promoter) and inducible promoters (e.g., the ADH2, GAL-1-10, GAL 7, PHO5, T7, T5, or metallothionine promoter), and a promoter-operator combination can be used to regulate transcription.

Exemplary eukaryotic promoters include the CMV promoter, the ASV promoter, the RSV-LTR promoter, the MMTV-LTR promoter, the early and late SV40 promoters, other viral promoters, promoters for the synthesis of glycolytic enzymes, and the hMTII promoter. In another embodiment, ribosome binding site sequences are also present. Other promoter systems are described in Chang et al., *Nature* 198: 1056 (1977), Goeddel, et al., *Nucleic Acids Res.* 8:4057 (1980), and Shimatake, et al., *Nature* 292:128 (1981), each of which is incorporated herein by reference.

The vectors can include other commonly used control sequences. For example, in one embodiment, the IMPDH-encoding nucleic acid has a terminator sequence for transcription termination (e.g., rrnBT1/T2 or HSP150 terminator). In another embodiment, the IMPDH-encoding nucleic acid molecule is spliced in frame with a transcriptional enhancer element. The vectors can also include bacterial origins of replication (e.g., ColE1) so that the vectors can be replicated in bacteria for ease of production of DNA, and can include sequences to stabilize messenger RNA.

Prokaryotic host cells include expression in gram negative or gram positive bacteria. Examples of eukaryotic host cells include any mammalian cell (e.g., COS, CHO, NIH/3T3, HeLa, Daudi, 293, 293-EBNA, and VERO cells), whether primary or immortalized, yeast cells such as *S. cerevisiae, S. pombe*, and *P. pastoris*, and insect cells, such as Sf9 cells (Smith et al., *J. Virol.* 46:584 (1983), Engelhard, et al., *Proc. Nat. Acad. Sci.* 91:3224-7 (1994), and U.S. Pat. No. 4,215, 051, all incorporated herein by reference), and fungal cells (e.g., *Trichoderma*). Eukaryotic host cells can be chosen to insure correct post-translational modification of proteins. Various host cell-vector systems are described in U.S. Pat. No. 6,451,572 and in PCT Publication No. WO 01/36607 A1, both incorporated herein by reference.

Figure 2:
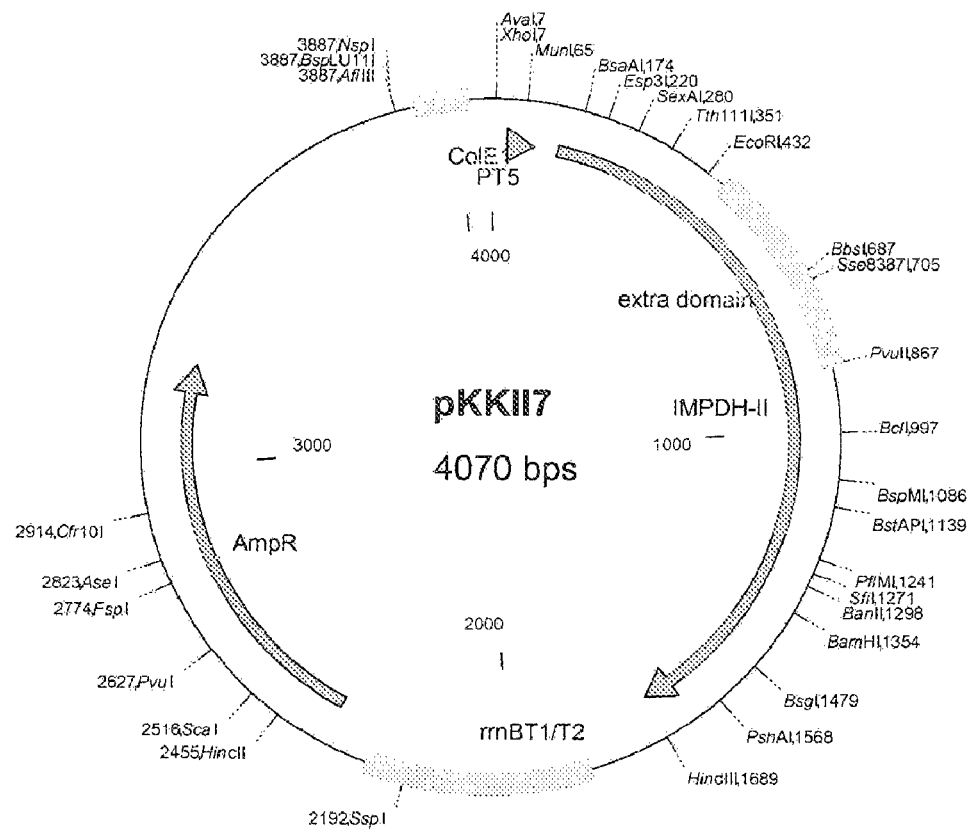
FIG. 2 shows a map of plasmid pKK117. The T5 promoter and lac operon (PT5) are located at nucleotides 30-90 in pKK117. The human IMPDH II coding sequence (1545 base pairs) is located at nucleotides 141-1685 in the plasmid and was inserted into the MunI and HindIII sites. The subdomain region is denominated the "extra domain." The transcription termination region (rrnBT1/T2) is located at nucleotides 1842-2268. The ampicillin resistance gene (AmpR) is located at nucleotides 2359-3219. The origin of replication (ColE1) is located at nucleotides 3924-4024 in pKK117. The coding sequence for the histidine tag (6 histidines) was inserted at nucleotide 144 in pKK117 into the 5'-end of the human wild-type, IMPDH type II coding sequence after the ATG start codon.

In another embodiment, a host cell-vector system for expressing histidine-tagged, modified IMPDH polypeptides is the pKK117 vector-*E. coli* H712 system described herein. FIG. 2 shows a map of plasmid pKK117. pKK117 contains the T5 promoter and lac operon (PT5) and these regulatory sequences are located at nucleotides 30-90 in pKK117. The human IMPDH II coding sequence (SEQ ID NO: 9; 1545 base pairs) was inserted at nucleotides 141-1685 in the plasmid. A transcription termination region (rrnBT1/T2) is located at nucleotides 1842-2268, and an ampicillin resistance gene (AmpR) is located at nucleotides 2359-3219. An origin of replication (ColE 1) for replication of pKK17 in bacteria is located at nucleotides 3924-4024. The coding sequence for the histidine tag (SEQ ID NO: 1; 6 histidines) was inserted at nucleotide 144 in pKK117 into the 5'-end of the human wild-type, IMPDH type II coding sequence after the ATG start codon. In the examples described herein, site-directed mutagenesis using PCR was performed (see SEQ ID NOS: 3-8 for the sequence of the PCR primers) in pKK117 containing the coding sequence for the histidine-tagged, wild-type IMPDH polypeptide.

In one embodiment, host cells comprising the nucleic acid molecules described herein are provided. The host cell can be selected from the group consisting of a bacteria, a yeast, a mammalian cell, a fungal cell, and an insect cell. The host cells comprise a vector, plasmid, phagmid, or cosmid comprising the nucleic acid molecules described herein encoding histidine-tagged, modified IMPDH polypeptides, or fragments thereof. In another embodiment, a vector is provided comprising any of the nucleic acid molecules described herein encoding histidine-tagged, modified IMPDH polypeptides, or fragments thereof.

Host cells can be transformed or transfected with a vector construct comprising the nucleic acid molecule encoding the histidine-tagged, modified IMPDH polypeptide using any transformation or transfection procedure known to those skilled in the art. Such procedures include electroporation, protoplast transformation, microinjection, virus-mediated transfection, $CaPO_4$-mediated transfection, DEAE-dextran-mediated transfection, lipofection, and $CaCl_2$ shock. For other transformation and transfection procedures and other cloning techniques known in the art, including descriptions of host cell-vector systems, see Sambrook et al., "Molecular Cloning: A Laboratory Manual," 3rd Edition, Cold Spring Harbor Laboratory Press, (2001), incorporated herein by reference. Growth conditions for transformed or transfected prokaryotic or eukaryotic cells are known in the art.

The host cells with the nucleic acid molecule encoding the histidine-tagged, modified IMPDH polypeptide can be identified by techniques well-known in the art. For example, bacterial host cells with the nucleic acid molecule encoding the histidine-tagged, modified IMPDH polypeptide can be cloned to produce single colonies. The single colonies can be cultured and the bacterial host cells in the culture lysed, for example, by sonication, heat, or chemical treatment, such as with lysozyme or a detergent to release the DNA, and the homogenate centrifuged to remove cell debris. The DNA can be isolated using the technique described in more detail below or using any other technique known in the art. The isolated DNA can be analyzed by techniques known in the art, such as restriction enzyme analysis or sequencing, to determine if the DNA contains an insert encoding the desired histidine-tagged, modified IMPDH polypeptide. The bacteria containing DNA encoding the histidine-tagged, modified IMPDH polypeptide can then be cultured to express histidine-tagged, modified IMPDH polypeptides.

For expression of the histidine-tagged, modified IMPDH polypeptides, host cells are cultured under conditions suitable for expression such as those described in more detail below. The cultured cells are then lysed for example, by sonication, heat, or chemical treatment, such as with lysozyme or a detergent to release the expressed polypeptide, and the homogenate centrifuged to remove cell debris. Expression of the histidine-tagged, modified IMPDH polypeptides can be detected by methods known in the art. For example, the modified IMPDH polypeptides can be detected by Coomassie staining of SDS-PAGE gels, immunoblotting using antibodies that bind IMPDH, or by IMPDH activity assays.

The histidine-tagged, modified and histidine-tagged, wild-type IMPDH polypeptides can be purified by nickel chelate affinity chromatography as described below either alone or in combination with other conventional purification techniques. Such purification techniques include ammonium sulfate precipitation, gel filtration, ion exchange chromatography, DEAE-Sepharose column chromatography, affinity chromatography, such as by using IMP or anti-IMPDH antibodies, solvent-solvent extraction, ultrafiltration, and HPLC. The histidine tag can also be removed following nickel chelate affinity chromatography by enzyme-based methods known in the art, such as enterokinase cleavage, and the modified IMPDH polypeptides can be purified from the released tag using any of the above-described conventional techniques. In illustrative embodiments, purification means at least about 60% pure, at least about 70-80% pure, at least about 90% pure, or at least about 95% pure. For additional purification techniques that can be used, see R. Scopes, "Protein Purification, Principles and Practice," Third Edition, Springer-Verlag (1994), incorporated herein by reference. It should be understood that the purification methods described above for purification of histidine-tagged, modified IMPDH polypeptides or histidine-tagged, wild-type IMPDH polypeptides are nonlimiting and any purification techniques known to those skilled in the art can be used to purify the histidine-tagged, modified IMPDH polypeptides or histidine-tagged, wild-type IMPDH polypeptides. The IMPDH polypeptides can be concentrated, if necessary, by such techniques as, for example, ultrafiltration and tangential flow filtration.

Thus, in one embodiment a method is provided for producing the histidine-tagged, modified IMPDH polypeptides described herein. The method comprises the step of culturing the host cell transformed with a nucleic acid molecule encoding the histidine-tagged, modified IMPDH polypeptide. The transformed host cell is cultured under suitable conditions to produce the histidine-tagged, modified IMPDH polypeptide. The method further comprises the step of recovering, as described above, the histidine-tagged, modified IMPDH polypeptide expressed in the transformed host cell. A histidine-tagged, modified IMPDH polypeptide produced by this method is also provided.

The activity of wild-type, histidine-tagged wild-type, and histidine-tagged, modified IMPDH polypeptides can be assayed using the in vitro methods described herein, or by methods known in the art such as the methods described in Carr, et al., *J. Biol. Chem.* 268:27286-27290 (1993) and Xiang, et al., *J. Biol. Chem.* 271:1435-1440 (1996), incorporated herein by reference. For example, the activity of the wild-type, histidine-tagged wild-type, or histidine-tagged, modified IMPDH polypeptides can be measured by spectrophotometric measurements at 340 nm. In such an assay, the change in absorbance at 340 nm of NADH per unit time is measured, and the change in absorbance of NADH reflects the rate of formation of NADH by IMPDH. In another embodiment, the activity of the IMPDH polypeptides can be assayed by measuring the production of XMP and NADH from IMP and NAD, using HPLC and spectrophotometric assays (see Montero, C. et al., *Clinica Chemica Acta* 238:169-178 (1995), incorporated herein by reference).

Various formulations of the purified histidine-tagged, modified IMPDH polypeptides can be prepared. The modified IMPDH polypeptides can be formulated as, for example, powders or liquids through known processes. The IMPDH enzymes can be added to buffer solutions and can be stabilized through the addition of chemical agents (e.g., glycerol, polyethylene glycol, EDTA, other proteins, detergents, and the like). The modified IMPDH polypeptides can be stored at 4° C. or can be frozen for storage or can be lyophilized.

In one embodiment, kits useful for measuring the concentration of an IMPDH inhibitor or another analyte in a sample are provided. The IMPDH inhibitor can be a drug, a drug derivative, a hormone, a polypeptide, an oligonucleotide, or the like. The histidine-tagged, modified IMPDH polypeptides are a component of these kits for use in assays such as those described in U.S. Pat. Nos. 6,107,052 and 6,524,808, incorporated herein by reference. Briefly, in these assays a sample, such as, for example, urine, whole blood, plasma, serum, saliva, semen, stool, sputum, cerebral spinal fluid, tears, mucus, or the like, is analyzed to determine the levels of an IMPDH inhibitor, or a metabolite of the inhibitor, or another analyte in the sample.

In the assay, the change in absorbance at 340 nm of NADH per unit time is measured, and the change in absorbance of NADH reflects the rate of formation of NADH. MPA or another inhibitor of IMPDH, or another analyte can inhibit the formation of NADH and, thus, the concentration of MPA, an MPA metabolite, or another inhibitor of IMPDH in a sample is inversely proportional to the absorbance of NADH at 340 nm. Accordingly, the level of an IMPDH inhibitor (e.g., MPA) or another analyte in a sample can be determined using such an assay.

The kit can contain the histidine-tagged, modified IMPDH polypeptide, an IMP substrate, and NAD. The IMPDH, IMP and NAD are commonly combined with an appropriate buffer and other materials and then packaged. In one embodiment, the reagents can remain in liquid form. In another embodiment, the reagents can be lyophilized. A calibration reagent can also be included in the kit and "calibration reagent" means any standard or reference material containing a known amount of the inhibitor to be measured, such as MPA or its metabolites, another IMPDH inhibitor, or another analyte. The sample suspected of containing the inhibitor (e.g., MPA) and the calibration reagent are assayed under similar conditions. The inhibitor concentration is then calculated by comparing the results obtained for the unknown specimen with the results obtained for the standard.

Other materials that may be included in the kits are, for example, buffers, stabilizers for the assay medium and the assay components, additional proteins, such as albumin, or surfactants, particularly non-ionic surfactants, or the like.

The histidine-tagged, modified IMPDH polypeptides described herein can be used, not only in assays for monitoring the levels of IMPDH inhibitors, but are also important for other clinical and research applications. For example, the histidine-tagged, modified IMPDH polypeptides can be used for the identification of naturally-occurring IMPDH inhibitors or other IMPDH-binding ligands, or for the design of synthetic inhibitors useful for cancer and immunosuppressive therapies, and for determining the sensitivity of IMPDH to these inhibitors.

The histidine-tagged, modified IMPDH polypeptides may also be used to elicit monoclonal or polyclonal antibodies, or fragments thereof (e.g., Fab, $F(ab')_2$, Fv fragments, or fusion proteins), by methods known in the art. In one embodiment, humanized antibodies for therapeutic applications can be produced. In another embodiment, the antibodies may be labeled with a detectable marker for use, for example, in diagnostic assays, or may be used for the purification of IMPDH.

The examples that follow are for illustrative purposes only and are not intended in any way to limit the scope of the invention.

Specific Embodiments

In the examples that follow, boldface numbers refer to the corresponding structure in the drawings.

EXAMPLE 1

Modification of Wild-Type Human Type II IMPDH

The wild-type human type II IMPDH sequence (SEQ ID NO: 9) was cloned into pKK117 (also denominated pKK/T7; see FIG. 2) at the site by cloning techniques known in the art. The wild-type IMPDH II sequence was modified to encode a 6-histidine tag at the 5'-end of the wild-type IMPDH II sequence by inserting the sequence shown in SEQ ID NO: 1 into the wild-type IMPDH II sequence in pKK117 after the ATG start codon by PCR using the primers shown in SEQ ID NO: 1 and SEQ ID NO: 2. The QuikChange™ Site-Directed Mutagenesis Kit (Stratagene, La Jolla, Calif.) was used and the primer design and the protocol for PCR were essentially as described in the instruction manual for the QuikChange™ Site-Directed Mutagenesis Kit. The primers were synthesized and purified by Commonwealth Biotechnologies, Inc., Richmond, Va.

Briefly, the PCR protocol was as follows. The PCR reactions contained 2 μL of double-stranded pKK117 DNA with the IMPDH II sequence inserted into the plasmid (the 2 μL volume contained 5, 10, 20, or 50 ng of plasmid DNA in TE buffer), 5 μL of 10× reaction buffer, 125 ng of each primer in TE buffer (2 μL each), 1 μL of dNTP mix, and ddH$_2$O (37 μL). PfuTurbo DNA polymerase (2.5 U/μL; 1 μL) was added to achieve a final volume of 50 μL, and each reaction was overlaid with 30 μL of mineral oil. The temperature cycling parameters were, for segment 1, one cycle at 95° C. for 30 seconds and, for segment 2, 18 cycles at 95° C. for 30 seconds and 68° C. for 12 minutes. After the PCR reaction, the reaction mixtures were cooled to 4° C. A control reaction using the pWhitescript plasmid and PCR primers provided in the QuikChange™ Site-Directed Mutagenesis Kit was also performed.

The PCR products were then digested with Dpn I by adding 1 μL of Dpn I to the reaction mixtures by pipetting below the mineral oil overlay, mixing the reaction mixtures, and incubating each reaction mixture at 37° C. for 1 hour to digest the plasmid DNA. Dpn I digests the parental, non-mutated plasmid DNA, but not the mutated plasmid DNA.

The PCR product is in the form of nicked, relaxed dsDNA. XL-1 Blue supercompetent cells (provided with the QuikChange™ Site-Directed Mutagenesis Kit) can take up the nicked, relaxed dsDNA and can repair the nicks. XL-1 Blue supercompetent cells were transformed with the mutated plasmids as follows. XL-1 Blue supercompetent cells were thawed on ice and kept at 4° C. The supercompetent cells were aliquotted (50 µL) into prechilled Falcon 2059 polypropylene tubes. An aliquot (1 µL) of the Dpn I digested DNA from each control and sample tube was transferred to separate aliquots of supercompetent cells. The transformation reactions were mixed and incubated at 4° C. for 30 minutes. The reaction mixtures were then heated at 42° C. for 45 seconds and incubated on ice for 2 minutes. NZY broth (42° C.; 0.5 ml) was added to each reaction mixture and the reactions were incubated at 37° C. with shaking (225-250 rpm) for 1 hour.

The transformation reactions were separately plated (250 µL) on LB agar plates with X-gal and IPTG with 100 µg/mL of ampicillin prepared as described in the instruction manual for the QuikChange™ Site-Directed Mutagenesis Kit. The plates were incubated at 37° C. for at least 16 hours. Single colonies were picked and grown overnight in LB broth with 100 µg/mL of ampicillin at 37° C. and with shaking at 225 rpm to expand the cultures. The overnight cultures were centrifuged at 4400×g for 30 minutes to the pellet cells, and the supernatants were discarded.

The bacteria were lysed and plasmid DNA was isolated from the XL-1 Blue cells using the QIAprep® kit (Qiagen, Valencia, Calif.) according to the kit instruction manual. Restriction enzyme digests were done to identify clones in which the coding sequence for the 6-histidine tag had been incorporated. The resulting digests were analyzed using 4-20% TBE gradient gels (1.0 mm thick; Invitrogen Cat. No. EC62252) and TBE running buffers (Invitrogen Cat. Nos. LC6678 and LC2675) according to procedures known the art. A 100 bp ladder (Gibco Cat. No. 15628-019) and a DNA silver stain kit (Pharmacia Cat. No. 17-6000-30) were used.

A protocol similar to that described above (QuikChange™ Site-Directed Mutagenesis Kit) was used to modify the subdomain in each of the histidine-tagged, modified IMPDH-encoding nucleotides described herein (i.e., Δ 2B+AH clone A, (Δ 3+1A)+AH clone A, Δ 1,2A+AH clone B, Δ 3B+AH clone B, and (Δ 2+1A)+AH clone B). The DNA used for PCR was the plasmid DNA isolated from XL-1 Blue cells using the QIAprep® kit. The wild-type IMPDH II sequence that had been modified to encode a 6-histidine tag at the 5'-end of the IMPDH II sequence was further modified in the subdomain region for each of the clones by PCR (using the IMPDH II sequence that had been modified to encode a 6-histidine tag at the 5'-end in pKK117 and using the primers shown in SEQ ID NOS: 3-8). The protocol was as described above except that the temperature cycling parameters for the PCR reaction were, for segment 2, 18 cycles at 95° C. for 30 seconds and 64° C. for 12 minutes.

Protocols similar to those described above, including transformation of supercompetent XL-1 Blue cells, lysis of the bacterial cells, and isolation of DNA using a QIAprep®) kit, were used to isolate clones positive for the desired IMPDH modifications, except that positive clones were confirmed by sequencing performed by Qiagen, Bothell, Wash., rather than by restriction enzyme digestion.

EXAMPLE 2

Transformation of E. coli H712

E. coli H712 (Yale University) was transformed and was used for expression of the histidine-tagged, modified IMPDH polypeptides, and for expression of the wild-type and histidine-tagged polypeptides. The DNA used for transformation of E. coli H712 was the plasmid DNA from positive clones isolated using the QIAprep® kit (Qiagen, Valencia, Calif.) or pKK117 plasmid with an insert encoding the wild-type polypeptide.

E. coli H712 were made competent by the method of Chung, et al., *Proc. Natl. Acad. Sci.* 86:2172 (1989), incorporated herein by reference, with modifications. Briefly, a fresh overnight culture of E. coli H712 in LB broth was diluted 1:50 into warmed LB broth to a final volume of 60 ml. The culture was incubated at 37° C. with shaking at 225 rpm until the culture reached an $OD_{600}$nm of about 0.3-0.4. The 60 mL culture was centrifuged for 15 minutes at 4100×g and the pellet was resuspended in 6 mL of cold TSS (LB broth, 10% PEG (MW 8000), 5% DMSO, 42 mM $MgCl_2$). Aliquots of the resuspended cells (0.1 ml) were prepared in cryovials in a bath of liquid nitrogen, and the cells were stored at −70° C.

E. coli H712 competent cells were transformed as follows. Tubes of competent cells were thawed on ice. A 1 µL aliquot of each purified plasmid was added to separate tubes and the liquid was gently mixed. The transformation mixtures were incubated on ice for 30 minutes. Preheated (42° C.) NZYM broth was added (0.5 ml) and the cells were heat shocked at 42° C. for 2 minutes. The cells were then immediately put back on ice for 2 minutes. Preheated (37° C.) NZYM broth (0.9 ml) was then added and the liquid was gently mixed. The transformation mixtures were incubated at 37° C. with shaking at 225 rpm for 30 minutes. Aliquots (20 µL) were then spread on agar plates (LB agar+100 µg/mL of ampicillin). The plates were incubated at 37° C. overnight. Colonies were picked, cultures were grown overnight, and glycerol stocks were prepared.

EXAMPLE 3

Expression of IMPDH Using E. coli H712

An overnight culture was grown from frozen glycerol stocks at 37° C. with shaking. The cells were grown in Terrific Broth+M9 Minimal Medium Salts, 2% Glucose, and 100 µg/mL of ampicillin. The cells were then diluted 1:1000 into fresh medium with IPTG (0.5 mM). The cultures were grown for 22 hours at 37° C. with shaking. The cells were harvested by centrifugation (4100×g for 30 minutes), washed with 0.9% NaCl, centrifuged again, and stored at −70° C.

The cells were thawed and lysed by adding 4.5 mL of lysis buffer per gram of cells. The lysis buffer was 10 mM Tris Base, 7.5 mM TCEP-HCl, Complete EDTA-free protease inhibitor (Roche Diagnostics) at the recommended concentration, 500 mM KCl, and 10 mM imidazole, pH 8.0). The solution was mixed until the entire pellet was in solution. Lysozyme 20,000 U/mL (Epicenter Cat. No. R1810M) was then added and the solution was mixed for 30 minutes. Benzonase (1 µl/ml; Novagen lysis solution Cat. No. 70746) was added and the solution was mixed for 30 minutes. Two parts of lysis dilution buffer were then added per one part of the lysate. The lysis dilution buffer was 20 mM $NaPO_4$, 7.5 mM TCEP-HCl, 0.5M KCl, 6.0M urea, 20 mM imidazole, and 0.3% NP-40, pH 8.0. The lysate was mixed for at least 30 minutes, and stored overnight in the cold at a temperature higher than 4° C. The lysate was centrifuged at 20,000×g for 30 minutes, and the supernatant was retained, adjusted to pH to 8.0, and filtered using a cellulose acetate filter.

EXAMPLE 4

Purification of IMPDH Isolated from *E. coli* H712

The histidine-tagged, modified IMPDH polypeptides and the wild-type histidine-tagged IMPDH polypeptides were purified by nickel chelate affinity chromatography followed by application of the eluted protein to a desalting column using procedures known in the art.

Nickel Chelate Affinity Chromatography

Nickel-resin can be obtained, for example, from Pharmacia (XK 26 column) and Qiagen (Valencia, CA; Ni-NTA Superflow Resin). The following purification protocols are applicable to nickel chelate affinity resins from Pharmacia or Qiagen. All buffers were degassed before use.

Buffers

Sample dilution buffer: 20 mM NaPO$_4$, 7.5 mM TCEP-HCl, 0.5M KCl, 6M urea, 0.02M imidazole, and 0.3% NP-40, pH 8.0.

Equilibration/binding/wash buffer: 20 mM NaPO$_4$, 7.5 mM TCEP-HCl, 0.5 M KCl, 4M urea, 0.02M imidazole, and 0.175% NP-40, pH 8.0.

Wash buffer (Qiagen only): 20 mM NaPO$_4$, 7.5 mM TCEP-HCl, 0.5M KCl, 0.02M imidazole, and 0.175% NP-40, pH 8.0.

Elution buffer A (Qiagen only): 20 mM NaPO$_4$, 7.5 mM TCEP-HCl, 0.5M KCl, 0.05M imidazole, and 0.175% NP-40, pH 8.0.

Elution buffer B: 20 mM NaPO$_4$, 7.5 mM TCEP-HCl, 0.5M KCl, 0.1M imidazole, and 0.175% NP-40, pH 8.0.

Elution buffer C (Qiagen only): 20 mM NaPO$_4$, 7.5 mM TCEP-HCl, 0.5M KCl, 0.2M imidazole, and 0.175% NP-40, pH 8.0.

Elution buffer D (Pharmacia only): 20 mM NaPO$_4$, 7.5 mM TCEP-HCl, 0.5M KCl, 0.2M imidazole, and 0.175% NP-40, pH 8.0.

| | Purification procedures | |
|---|---|---|
| Step | Pharmacia resin (100 mL column) | Qiagen resin (25 mL column) |
| Load | 10 ml/minute | 3 ml/minute (to not exceed pressure specifications) |
| Wash 1 | Equilibration/binding/wash buffer, 10 ml/minute | Equilibration/binding/wash buffer, 3 ml/minute |
| Wash 2 | N/A | Wash buffer, no urea, 3 ml/minute |
| Elution 1 | Elution buffer B (0.1M imidazole), 10 ml/minute | Elution buffer A (0.05M imidazole), 3 ml/minute |
| Elution 2 | Elution buffer D (0.3M imidazole), 10 ml/minute | Elution buffer B (0.1M imidazole), 3 ml/minute |
| Elution 3 | N/A | Elution buffer C (0.2M imidazole), 3 ml/minute |
| Product | Elutes in 0.3M imidazole | Elutes in 0.1M imidazole |

Desalting Column Chromatography

Materials

HiPrep 26/10 Desalting column, Pharmacia (Cat. No. 17-5087-01)

Desalting Buffer: 0.437M TAPSO, 25.8M potassium acetate, 4.32 mM IMP, 7.5 mM TCEP-HCl, 0.2% Suttocide A, and 0.175% NP-40, pH 8.0.

Desalting Procedure

All buffers were degassed before use. The desalting column must be well equilibrated and running (zeroed) at time of loading. As the protein eluted from the nickel chelate affinity column was applied to the desalting column, the fraction collector was set to collect 5 mL fractions. When the enzyme peak had eluted from the column, the fraction collector was turned off and the flow was diverted to waste. The peak fractions were pooled and assayed. A shoulder or a second peak was observed after the eluted IMPDH, but there was no activity in this shoulder and it was not pooled. Columns fractions with IMPDH were identified by measuring enzyme activity in the fractions using the assay described in Example 5. The purified IMPDH was stored at 4° C. or −20° C.

EXAMPLE 5

IMPDH Enzyme Activity Assay

The column fractions were assayed for enzyme activity as follows. The specific activity of purified IMPDH was also determined. Enzyme activity combined with determination of protein concentration provides a means of determining specific activity of the purified protein, which is an indication of degree of aggregation.

Enzyme Assay Materials

Diluent: 100 mM TAPSO, 3.1 mM TCEP-HCl, 100 mM KCl, 0.2 mM IMP, pH 8.0.

Reaction Buffer: 100 mM TAPSO, 3.1 mM TCEP-HCl, 10 mM KCl, 0.2 mM IMP, 0.4 mM NAD, pH 8.0.

Enzyme Assay Equipment

Cary 50 BioSpec temperature controlled UV/vis spectrophotometer

Enzyme Assay Procedure

The purified enzyme was diluted and placed into a cuvette, the cuvette was placed into the cuvette carrier, and the solution was equilibrated to 37° C. The assay reaction buffer (990 μL) was added to a separate cuvette and the cuvette was covered and placed in the cuvette carrier. The solution was equilibrated to 37° C. Warmed sample (115.5 μL) was added to the warmed reaction buffer and the solution was mixed by inversion and placed back into the spectrophotometer. The reaction was immediately monitored at 340 nm by taking an absorbance reading every 10 seconds for 3 minutes. Enzyme activity was calculated as follows:

$$\frac{\Delta \text{ absorbance}}{6.22} \times \text{dilution factor} \times \frac{\text{total volume}}{\text{sample volume}} = \text{total enzyme activity}$$

Protein levels were determined using the Compat-Able™ Protein Assay Preparation Reagent Set (Pierce Cat. No. 23215) or the Protein Assay ELC (Roche Diagnostics Cat. No. 1767003). Specific activity is defined as activity per mass of protein, and was approximately 1 unit/mg for the modified IMPDH II polypeptides.

EXAMPLE 7

IMPDH Rate Stability Assay

Figure 18:
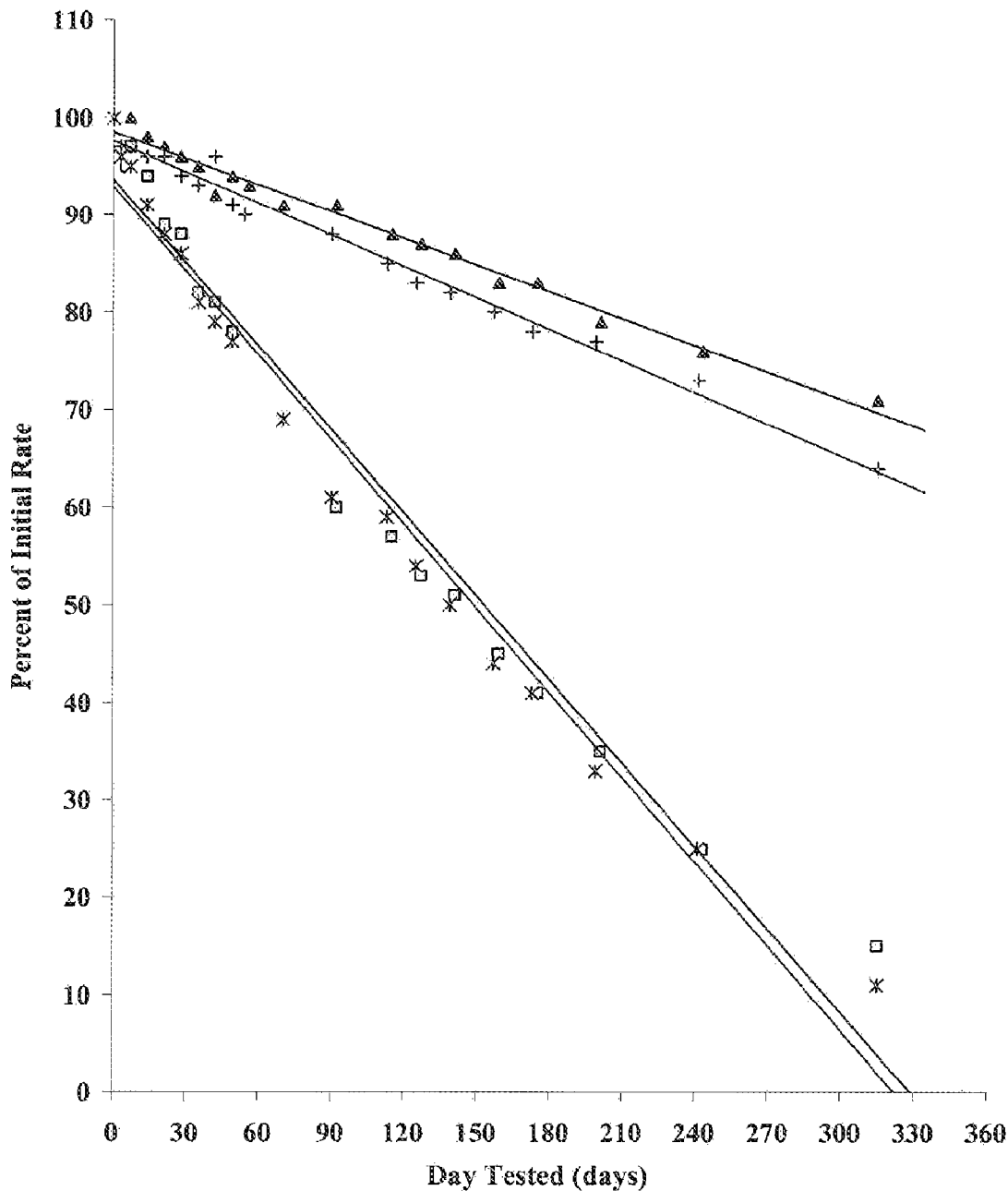
FIG. 18 shows rate stability data (i.e., % remaining IMPDH activity/time) for human wild-type, IMPDH type II as a percentage of the initial rate (x-axis) versus the day tested (y-axis). IMPDH activity was tested using buffer system R1 C(1) (▲, □) or R1 F (+, ✳) and was tested at 4° C. (▲, +) and 25° C. (□, ✳).
Figure 19:
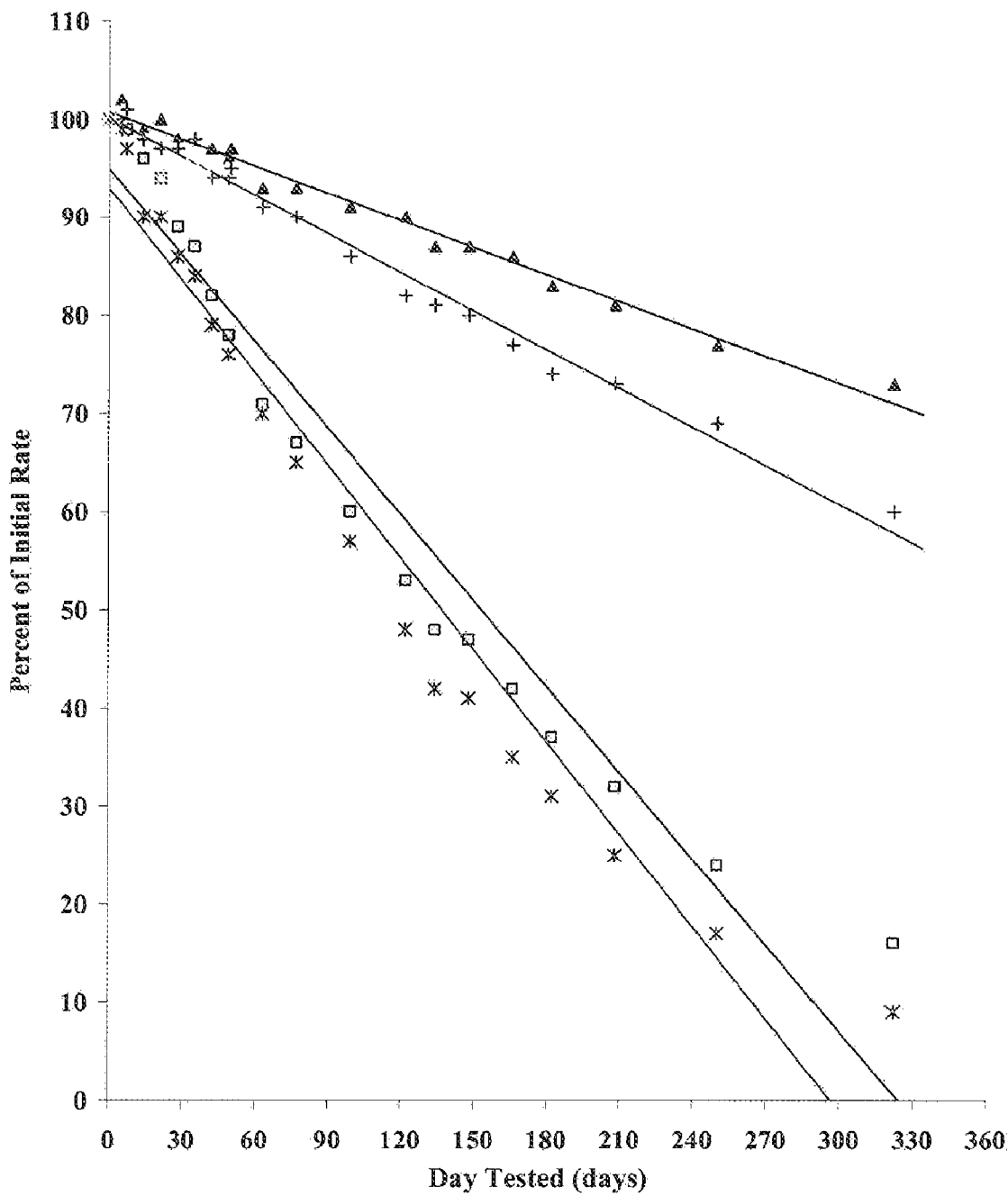
FIG. 19 shows rate stability data (i.e., % remaining IMPDH activity/time) for histidine-tagged human IMPDH type II as a percentage of the initial rate (x-axis) versus the day tested (y-axis). Histidine-tagged IMPDH activity was tested using buffer system R1 C(1) (▲, □) or R1 F (+, ✳) and was tested at 4° C. (▲, +) and 25° C. (□, ✳).
Figure 20:
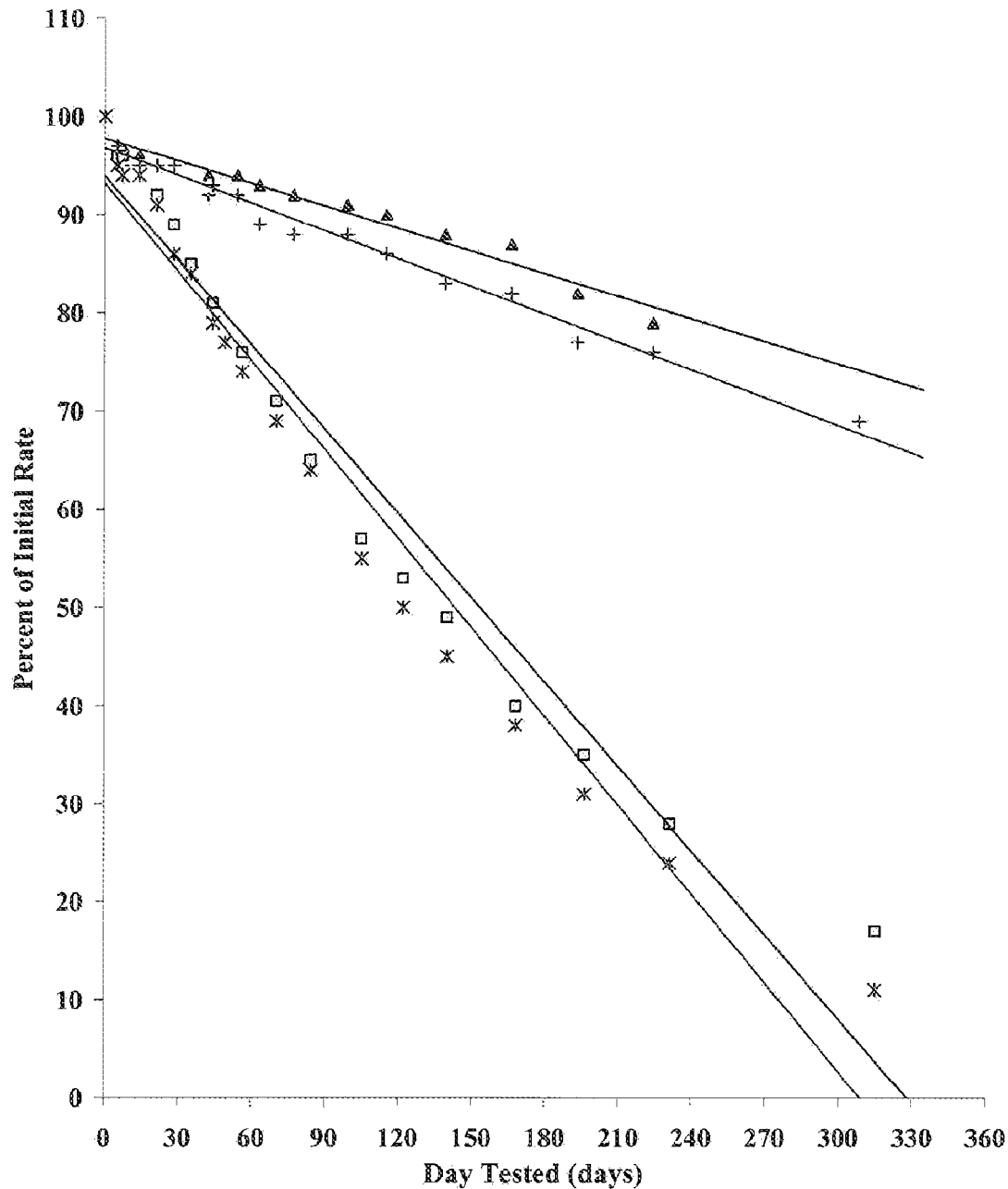
FIG. 20 shows rate stability data (i.e., % remaining IMPDH activity/time) for IMPDH type II Δ 2B+AH clone A as a percentage of the initial rate (x-axis) versus the day tested (y-axis). IMPDH type II Δ 2B+AH clone A activity was tested using buffer system R1 C(1) (▲, ☐) or R1 F (+, Ж) and was tested at 4° C. (▲, +) and 25° C. (☐, Ж).
Figure 21:
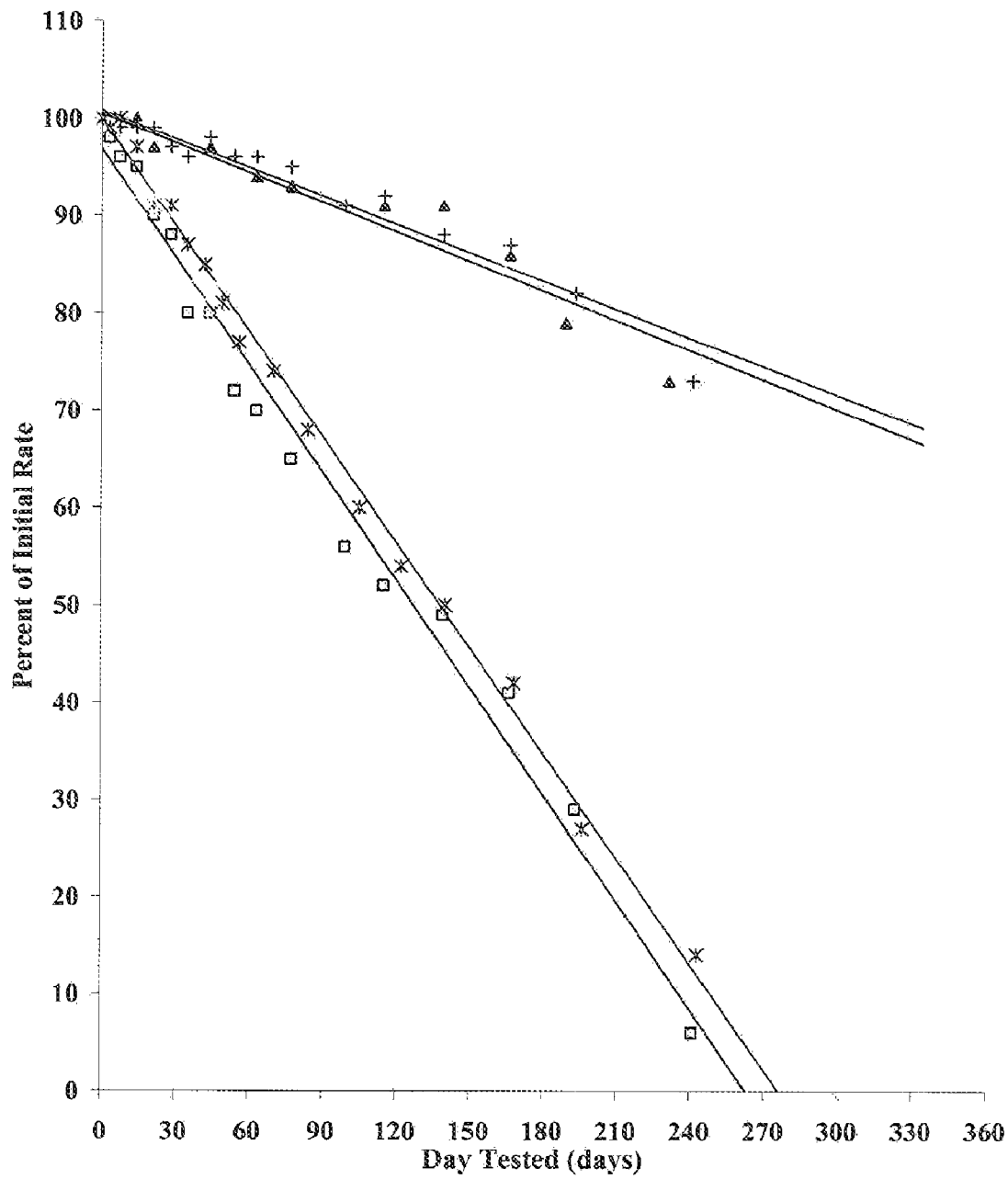
FIG. 21 shows rate stability data (i.e., % remaining IMPDH activity/time) for human IMPDH type II (Δ 3+1A)+AH clone A as a percentage of the initial rate (x-axis) versus the day tested (y-axis). IMPDH type II (Δ 3+1A)+AH clone A activity was tested using buffer system R1 C(1) (▲, ☐) or R1 F (+, Ж) and was tested at 4° C. (▲, +) and 25° C. (☐, Ж).
Figure 22:
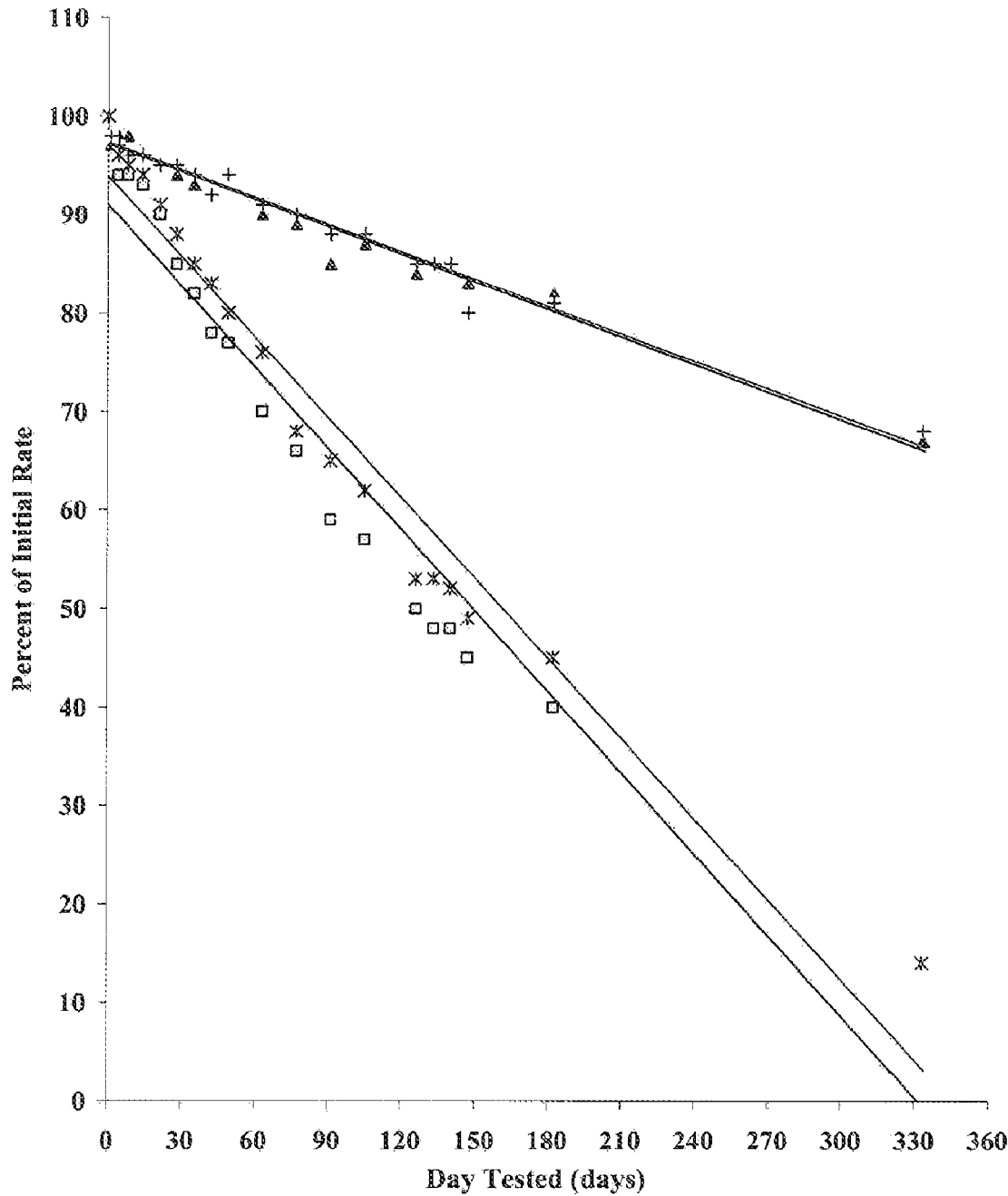
FIG. 22 shows rate stability data (i.e., % remaining IMPDH activity/time) for human IMPDH type II Δ 1,2A+AH clone B as a percentage of the initial rate (x-axis) versus the day tested (y-axis). IMPDH type II Δ 1,2A+AH clone B activity was tested using buffer system R1 C(1) (▲, ☐) or R1 F (+, Ж) and was tested at 4° C. (▲, +) and 25° C. (☐, Ж).
Figure 23:
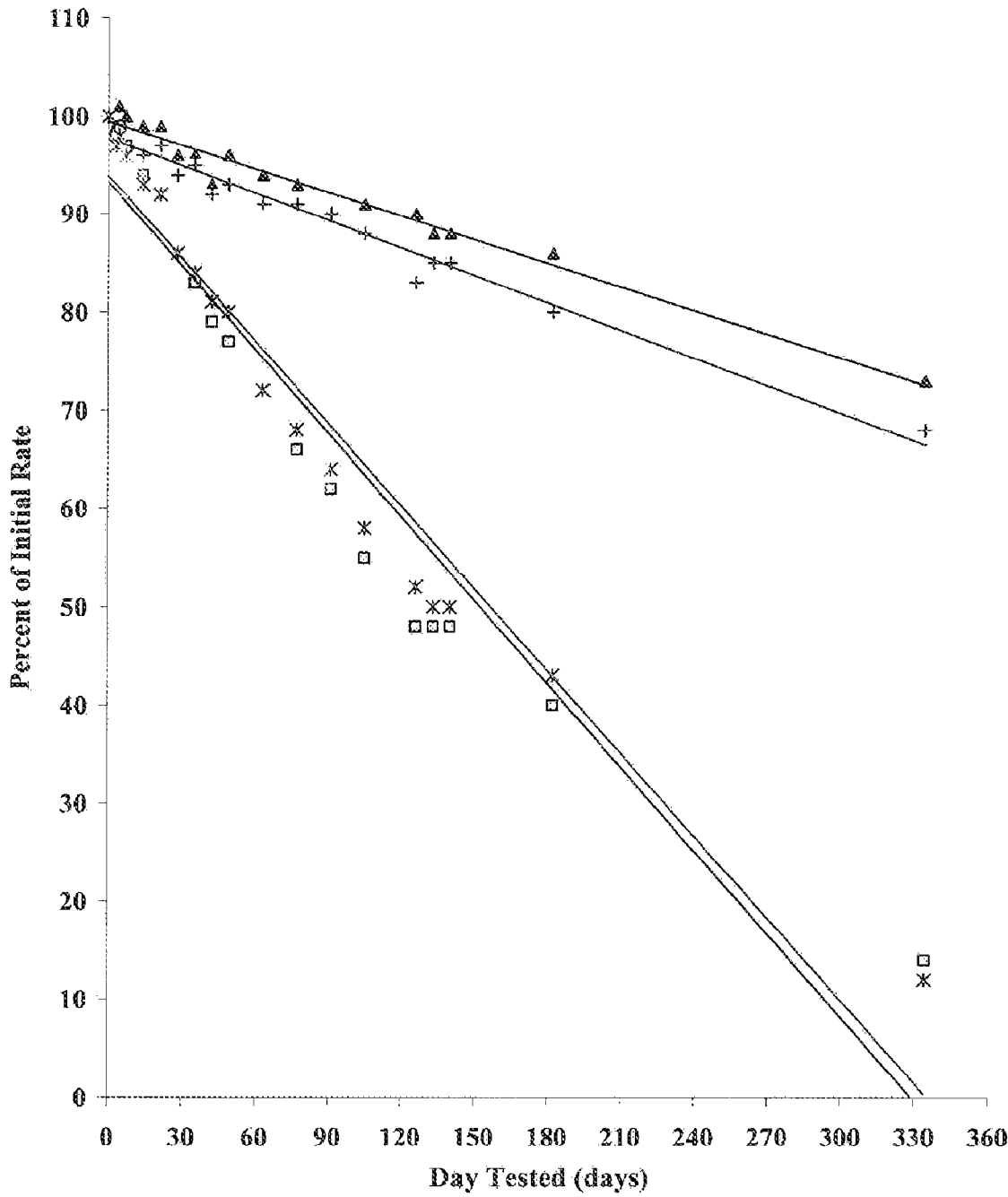
FIG. 23 shows rate stability data (i.e., % remaining IMPDH activity/time) for human IMPDH type II Δ 3B+AH clone B as a percentage of the initial rate (x-axis) versus the day tested (y-axis). IMPDH type II Δ 3B+AH clone B activity was tested using buffer system R1 C(1) (▲, ☐) or R1 F (+, Ж) and was tested at 4° C. (▲, +) and 25° C. (☐, Ж).
Figure 24:
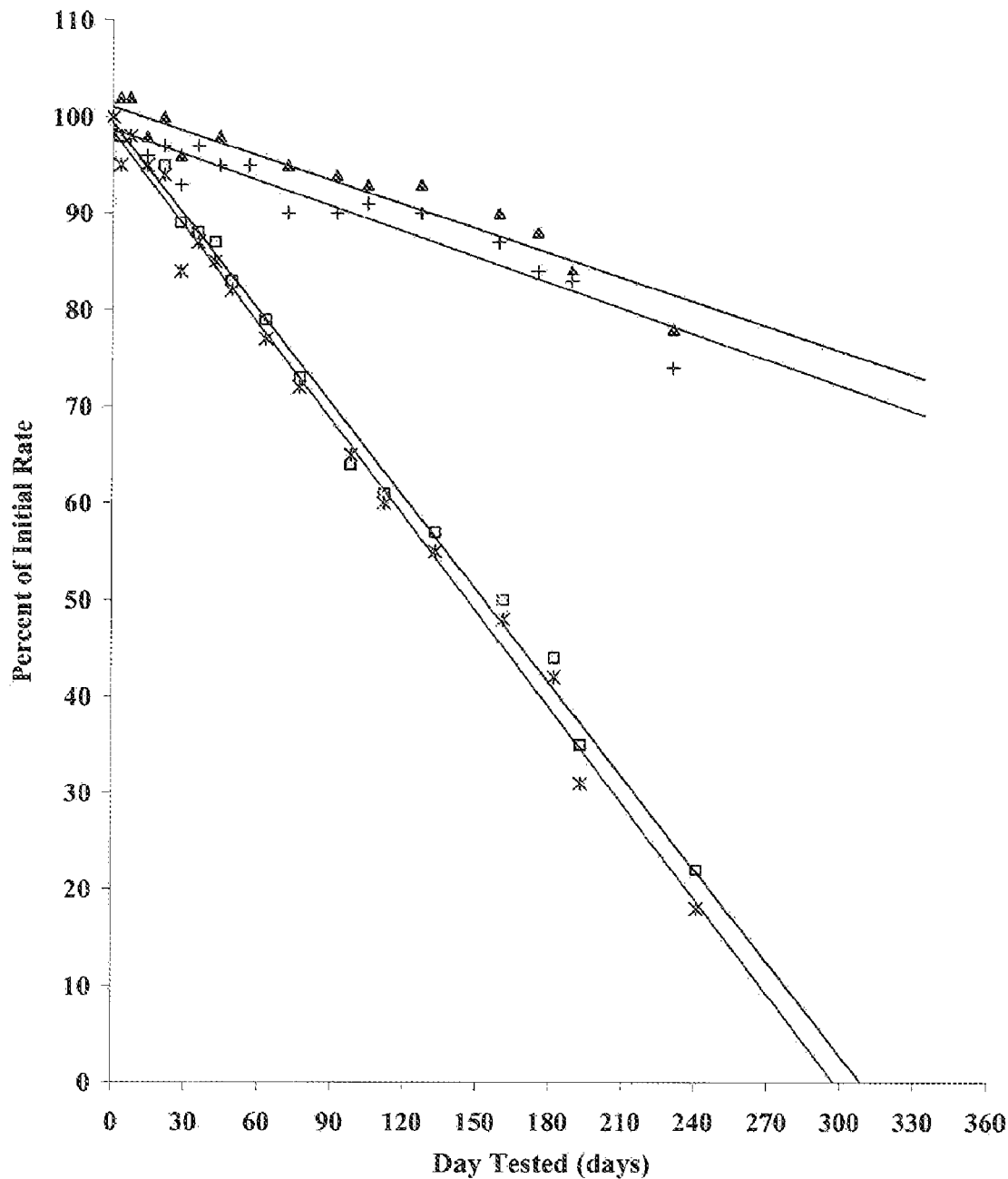
FIG. 24 shows rate stability data (i.e., % remaining IMPDH activity/time) for human IMPDH type II (Δ 2+1A)+AH clone B as a percentage of the initial rate (x-axis) versus the day tested (y-axis). IMPDH type II (Δ 2+1A)+AH clone B activity was tested using buffer system R1 C(1) (▲, ☐) or R1 F (+, Ж) and was tested at 4° C. (▲, +) and 25° C. (☐, Ж).

The rate stabilities of the histidine-tagged, modified IMPDH enzymes (FIGS. 20-24) were measured to compare the rate stability of the histidine-tagged, modified enzymes (i.e., modified in the subdomain) to the rate stability of the histidine-tagged, wild-type IMPDH enzyme (FIG. 19). The rate stability of the wild-type enzyme without a tag was also measured (FIG. 18). The rate stabilities were measured as follows:

Buffers

R1 C(1): 0.437M TAPSO, 0.0258M sodium acetate, 2.35 mM TCEP, 4.32 mM IMP, 0.3 mM disodium EDTA, 0.72 mM sodium phosphate, 10.7 mM KCl, and 0.1% Suttocide A, pH 8.0. An alternative buffer R1 C(1) formulation is 0.437M TAPSO, 25.8M potassium acetate, 7.5 mM TCEP, 4.32 mM IMP, 0.175% NP40, and 0.2% Suttocide A, pH 8.0.

R1 F: 0.116M TAPSO, 0.347M sodium acetate, 2.35 mM TCEP, 4.32 mM IMP, 3.51 mM disodium EDTA, 0.72 mM sodium phosphate, 10.7 mM KCl, and 0.05% Suttocide A, pH 8.0.

R2: 2.5 mM NAD, 0.175% NP40, and 0.05% Suttocide A, pH 6.0. An alternative R2 formulation is 0.1M ACES, 10 mM NAD, 7.5 mM TCEP, 0.175% NP40, and 0.05% Suttocide A, pH 6.0.

ACES=N-(2-acetamido)-2-aminoethanesulfonic acid or N-(carbamoylmethyl)-2-aminoethanesulfonic acid or N-(carbamoylmethyl)taurine or 2-(carbamoylmethyl-amino) ethanesulfonic acid.

TAPSO=N-[tris(hydroxymethyl)methyl]-3-amino-2-hydroxy-propanesulfonic acid or 2-hydroxy-3-[tris(hydroxymethyl)methylamino]-1-propanesulfonic acid.

TCEP=Tris(2-carboxyethyl)phosphine or 3,3',3"-phosphinidyne-tripropionic acid.

TCEP-HCl=Tris(2-carboxyethyl)phosphine hydrochloride or 3,3',3"-phosphinidyne-tripropionic acid hydrochloride.

Enzyme Assay Procedure

The rate stability assays were done at 4° C. and 37° C. The rates were compared to the t=0, 4° C. rate and either buffer R1 C(1) or R1 F was used. The rate stability assays were run on a Hitachi 917 analyzer with the following parameters:

Rate A, 10 minutes, read window 28-33

Primary wavelength: 340 nm

Secondary wavelength: 700 nm

Sample volume: 2 μL

R1 volume: 167 μL

R2 volume: 33 μL

Calibration type: spline

As discussed above, the rate stabilities of the histidine-tagged, modified IMPDH enzymes (FIGS. 20-24) were measured to compare the rate stability of the histidine-tagged, modified enzymes (i.e., modified in the subdomain) to the rate stability of the histidine-tagged, wild-type IMPDH enzyme (FIG. 19). The results depicted in FIGS. 18-24 show that the rate stability of the histidine-tagged, modified IMPDH polypeptides is approximately equal to the wild-type protein (i.e., the histidine-tagged, modified IMPDH polypeptides do not exhibit the decreased rate stability observed for histidine-tagged IMPDH polypeptides that have not been modified in the subdomain). Accordingly, modification of a histidine-tagged IMPDH polypeptide in the subdomain, as described herein, results in maintenance of rate stability of the enzyme relative to the wild-type IMPDH enzyme.

What is claimed is:

1. A vector comprising a nucleic acid molecule which encodes a modified inosine-5'-monophosphate dehydrogenase (IMPDH) polypeptide comprising the modified polypeptide of SEQ ID) NO: 12, said modified polypeptide consisting of at least one ammo acid substitution at a position selected from the group consisting of 130, 132, 134, 140, 142, 155, 159, 167, and 173, wherein said substitution comprises replacement of a native amino acid with a negatively charged amino acid, said IMPDH polypeptide further comprising a histidine tag.

2. The vector or claim 1 wherein said modified IMPDH polypeptide comprises the amino acid sequence of SEQ ID) NO: 14.

3. The vector of claim 1 wherein said modified IMPDH polypeptide has the amino acid sequence selected from the group consisting, of SEQ ID NOS:14, 16, 18, 20, and 22.

4. The vector of claim 1 wherein one or more of the amino acids at positions 130, 132, 134, 140, 142, 155, 159, 167, and 173 are substituted with glutamic acid or aspartic acid.

5. The vector of claim 1 wherein two or more of the amino acids at positions 130, 132, 134, 140, 142, 155, 159, 167, and 173 are substituted with a negatively charged ammo acid.

6. The vector of claim 1 wherein two or more of the amino acids at positions 130, 132, 134, 140, 142, 155, 159, 167, and 173 are substituted with glutamic acid.

7. A host cell comprising the vector of claim 1, said host cell selected from the group consisting of bacteria, yeast, mammalian, fungal, and insect cells.

8. A host cell comprising the vector of claim 2, said host cell selected from the group consisting of bacteria, yeast, mammalian, fungal, and insect cells.

9. A host cell comprising the vector of claim 3, said host cell selected from the group consisting of bacteria, yeast, mammalian, fungal, and insect cells.

10. A host cell comprising the vector of claim 4, said host cell selected from the group consisting of bacteria, yeast, mammalian, fungal, and insect cells.

11. A host cell comprising the vector of claim 5, said host cell selected from the group consisting of bacteria, yeast, mammalian, fungal and insect cells.

12. A host cell comprising the vector of claim 6, said host cell selected from the group consisting of bacteria, yeast, mammalian, fungal, and insect cells.

13. A method for producing a modified inosine-5'-monophosphate dehydrogenase (IMPDH) polypeptide. said method comprising the steps of:
culturing the host cell of claim 7 under suitable conditions to produce said modified IMPDH polypeptide, and
recovering said mod tiled IMPDH polypeptide produced.

14. A method for producing a modified inosine-5'-monophosphate dehydrogenase (IMPDH) polypeptide, said method comprising the steps of:
culturing the host cell of claim 8 under suitable conditions to produce said modified IMPDH polypeptide, and
recovering said modified IMPDH polypeptide produced.

15. A method for producing a modified inosine-5'-monophosphate dehydrogenase (IMPDH) polypeptide, said method comprising the steps of:
culturing the host cell of claim 9 under suitable conditions to produce said modified IMPDH polypeptide, and
recovering said modified IMPDH polypeptide produced.

16. A method for producing a modified inosine-5'-monophosphate dehydrogenase (IMPDH) polypeptide, said method comprising the steps of: culturing the host cell of claim 10 tinder suitable conditions to produce said modified IMPDH polypeptide, and
recovering said modified IMPDH polypeptide produced.

17. A method for producing a modified inosine-5'-monophosphate dehydrogenase (IMPDH polypeptide, said method composing the steps of:
culturing the host cell of claim 11 under suitable conditions to produce said modified IMPDH polypeptide, and
recovering said modified IMPDH polypeptide produced.

18. A method for producing a modified inosine-5'-monophosphate dehydrogenase IMEPDH polypeptide, said method comprising the steps of: culturing the host cell of claim 12 under suitable conditions to produce said modified IMPDH polypeptide, and recovering said modified IMPDH polypeptide produced.

19. An isolated nucleic acid molecule encoding a modified inosine-5'-monophosphate dehydrogenase (IMPDH) polypeptide consisting of the modified polypeptide of SEQ ID NO: 12, said modified polypeptide consisting of at least one amino acid substitution at a position selected from the group consisting of 130, 132, 134, 140, 142, 155, 159, 167, and 173, wherein said substitution comprises replacement of a native amino acid with a negatively charged amino acid, said IMPDH polypeptide further comprising a histidine tag.

20. The isolated nucleic acid molecule of claim 19 Wherein said modified IMPDH polypeptide comprises the amino acid sequence of SEQ TI) NO: 14.

21. The isolated nucleic acid molecule of claim 19 wherein said modified IMPDH polypeptide has the amino acid sequence selected from the group consisting of SEQ ID) NOS: 14, 16, 18, 20, and 22.

22. The isolated nucleic acid molecule of claim 19 wherein one or more of the amino acids at positions 130, 132, 134, 140, 142, 155, 159, 167, and 173 of said IMPDH polypeptide are substituted with glutamic acid or aspartic acid.

23. The isolated nucleic acid molecule of claim 19 wherein two or more of the amino acids at positions 130, 132, 134, 140, 142, 155, 159, 167, and 1,73 of said IMPDH polypeptide are substituted with a negatively charged amino acid.

24. The isolated nucleic acid molecule of claim 19 wherein two or more of the amino acids positions 130, 132, 134, 140, 142, 155, 159, 167, and 173 are substituted with glutamic acid.

* * * * *